(12) United States Patent
Newell et al.

(10) Patent No.: US 11,323,776 B2
(45) Date of Patent: *May 3, 2022

(54) APPARATUS, SYSTEMS AND METHODS FOR GENERATING AN EMOTIONAL-BASED CONTENT RECOMMENDATION LIST

(71) Applicant: DISH Technologies L.L.C., Englewood, CO (US)

(72) Inventors: Nicholas Newell, Centennial, CO (US); Prakash Subramanian, Littleton, CO (US)

(73) Assignee: DISH Technologies L.L.C., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,003

(22) Filed: Aug. 11, 2020

(65) Prior Publication Data

US 2020/0374588 A1 Nov. 26, 2020

Related U.S. Application Data

(63) Continuation of application No. 16/127,814, filed on Sep. 11, 2018, now Pat. No. 10,764,641, which is a
(Continued)

(51) Int. Cl.
*H04N 21/466* (2011.01)
*A61B 5/16* (2006.01)
*A61B 5/374* (2021.01)
*A61B 5/378* (2021.01)
*A61B 5/00* (2006.01)
*H04N 21/422* (2011.01)
*H04N 21/442* (2011.01)
*H04N 21/45* (2011.01)
*H04N 21/8405* (2011.01)

(52) U.S. Cl.
CPC ........ *H04N 21/4667* (2013.01); *A61B 5/163* (2017.08); *A61B 5/165* (2013.01); *A61B 5/374* (2021.01); *A61B 5/378* (2021.01); *A61B 5/6803* (2013.01); *H04N 21/42201* (2013.01); *H04N 21/44218* (2013.01); *H04N 21/4532* (2013.01); *H04N 21/8405* (2013.01)

(58) Field of Classification Search
CPC ......... H04N 21/4667; H04N 21/42201; H04N 21/44218; H04N 21/4532; H04N 21/8405; H04N 21/44222; H04N 21/6582; H04N 21/25891; H04N 21/251; H04N 21/258; H04N 21/4508; H04N 21/466; H04H 60/33; H04H 60/46
See application file for complete search history.

(56) References Cited

U.S. PATENT DOCUMENTS 6,623,427 B2 9/2003 Mandigo
2009/0289895 A1 11/2009 Nakada et al.
(Continued)

FOREIGN PATENT DOCUMENTS

JP 2010 220151 9/2020

*Primary Examiner* — Alexander Gee
(74) *Attorney, Agent, or Firm* — Perkins Coie LLP

(57) ABSTRACT

Media content recommendation systems and methods are operable to recommend one or more media content events to a user based on identified changes in the user's emotional state during a life event that is experienced by the user.

20 Claims, 4 Drawing Sheets

Related U.S. Application Data continuation of application No. 15/833,370, filed on Dec. 6, 2017, now Pat. No. 10,091,554.

(56) References Cited

U.S. PATENT DOCUMENTS

| | | | |
|---|---|---|---|
| 2011/0247042 A1* | 10/2011 | Mallinson | H04N 21/44008 725/86 |
| 2013/0012829 A1* | 1/2013 | Jo | G06F 3/015 600/544 |
| 2014/0022157 A1* | 1/2014 | Lee | G06F 3/0481 345/156 |
| 2014/0282772 A1* | 9/2014 | Chen | H04N 21/42201 725/97 |
| 2014/0347265 A1* | 11/2014 | Aimone | H04W 4/029 345/156 |
| 2015/0029087 A1 | 1/2015 | Klappert et al. | |
| 2017/0311023 A1 | 10/2017 | Chen et al. | |
| 2018/0232608 A1* | 8/2018 | Pradeep | G01S 5/28 |

* cited by examiner

APPARATUS, SYSTEMS AND METHODS FOR GENERATING AN EMOTIONAL-BASED CONTENT RECOMMENDATION LIST

PRIORITY CLAIM

This patent application is a Continuation of U.S. Non-Provisional patent application Ser. No. 16/127,814, filed Sep. 11, 2018, entitled "APPARATUS, SYSTEMS AND METHODS FOR GENERATING AN EMOTIONAL-BASED CONTENT RECOMMENDATION LIST," which is a Continuation of U.S. Non-Provisional patent application Ser. No. 15/833,370, filed Dec. 6, 2017, entitled "APPARATUS, SYSTEMS AND METHODS FOR GENERATING AN EMOTIONAL-BASED CONTENT RECOMMENDATION LIST," now issued as U.S. Pat. No. 10,091,554 on Oct. 2, 2018, the contents of which are is incorporated herewith in their entireties.

BACKGROUND

Many prior art systems and processes determine user content preferences based on the user's prior viewing pattern and/or history. Typically, content (interchangeably referred to herein as a media content event) presents theme-based visual and audio content to a user for their enjoyment and/or for informative purposes. Examples of such theme-based content includes movies, films, serial programming, sporting events, documentaries, newscasts, religious programs, commercials (typically of short duration with advertising content), or the like. Serial programming may present a continuing plot and/or theme, often with the same cast of actors, in a sequential episode-by-episode basis that is available periodically. Advertisements, commercials or the like may be interspersed within the media content event. Content may also be audio only content, such as a song, concert, commentary, or the like.

As is well known in the arts, the user's prior viewing pattern and/or history can be analyzed to identify characteristics of the content that the user has previously viewed. Then, a comparison of the identified characteristics of the prior viewed content may be used to identify patterns of the user's viewing habits and/or preferences such that one or more particular genres of favored content can be identified. A genre is a category of artistic composition, as in audio visual content, music or literature, that is characterized by similarities in form, style, and/or subject matter. Such identified genre can then be defined as a user preference for that particular user.

The benefits of knowing user preferences are well known. For example, once user-preferred content that the user has not yet consumed is identified, the user can be informed about the availability of the identified user-preferred content. For example, a future scheduled broadcast of one or more of the identified user-preferred content can be indicated to the user who may then choose to view and/or record the content when the content is broadcast. Some systems may even automatically configure a user device to record the identified user-preferred content during the broadcast of the content. Alternatively, or additionally, one or more of the identified user-preferred content may be available on a pay for view basis, a rental, and/or on a premium based service. Here, the user may decide to pay to view and/or subscribe to a service to obtain access to the identified user-preferred content.

Such prior art systems and processes identify user preferences based on historical viewing patterns or activities of the user. That is, the prior art systems and processes determine user genre preferences based on "what" content the user has previously consumed (interchangeably referred to herein as "viewing" or the like).

A deficiency in such prior art systems and processes is that there is a likelihood in failing to identify particular content that the user may otherwise be interested in viewing when that content does not relate to an identified user genre preference determined from "what" content the user has previously consumed. More particularly, the prior art systems and processes have not determined "why" the user may prefer such genre-based content. That is, the user's personal experiences have not been taken into account during the determination of the user preference.

To illustrate, consider a user who has an identified user genre preference for action type content (action movies, action serial programs, or the like). This particular identified user genre preference is based upon the user having previously consumed a plurality of action genre content. Further, consider situations where the prior art systems and processes have not determined that the user might like to consume a media content event associated with a romantic comedy genre (since the user has not previously viewed, or has only previously viewed a relatively small number of, romantic drama genre content). Here, it is very likely that the prior art systems and processes may fail to identify and recommend a particular media content event that is classified, at least in part, to be a romantic drama genre media content event because this romantic comedy genre media content event is not associated with the action genre content that has been determined to be a user genre preference. However, it may be that the user may actually want to consume this particular media content event even though it is not one of the user's genre preferences.

Further, the particular media content event that is not recommended may have one or more story elements that may be of high interest to the user. A story element is a textual description of a thematic aspect of the media content event that includes the following components: the characters, the setting, the plot, the conflict and the resolution. Thus, the particular media content event would not be recommend to the user even though that particular media content event may have one or more story elements that are of high interest to the user.

Accordingly, there is a need in the art to improve prior art systems and processes that are limited to identifying user preferences based on "what" particular content the user has previously consumed.

SUMMARY

Media content recommendation systems and methods are operable to recommend one or more media content events to a user based on identified changes in the user's emotional state during a life event that is experienced by the user.

BRIEF DESCRIPTION OF THE DRAWINGS

Preferred and alternative embodiments are described in detail below with reference to the following drawings.

DETAILED DESCRIPTION

Figure 1:
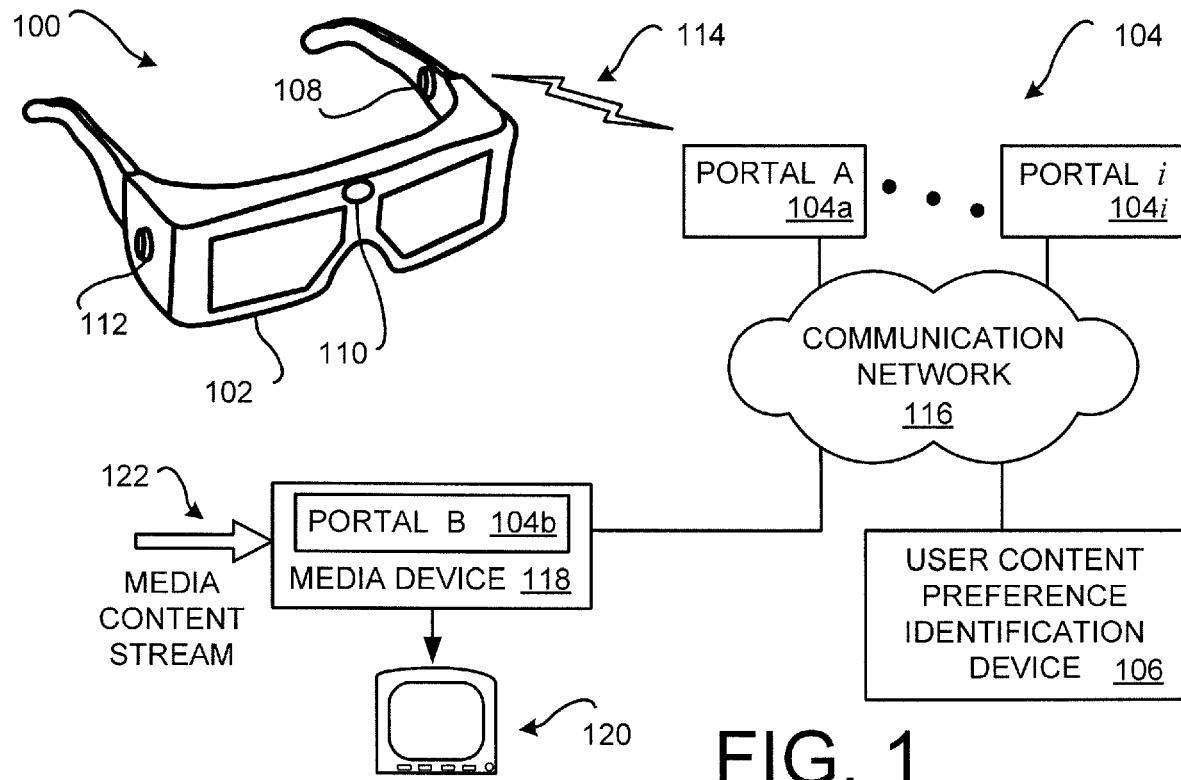
FIG. 1 is a block diagram of an embodiment of the user content preference identification system.

FIG. 1 is a block diagram of an embodiment of the user content preference identification system 100. The exemplary user content preference identification system 100 comprises an emotional state monitor (ESM) 102, a plurality of electronic portal devices 104, and at least one user content preference identification device 106.

An exemplary embodiment of the user content preference identification system 100 identifies at least one media content event based on the user's prior viewing emotional experiences and/or based on the user's past life experiences that elicited a change in the user's emotional state. That is, embodiments of the user content preference identification system 100 initially determine "why" a user may have an emotional preference, emotional dislike, and/or emotional disinterest based on the user's past emotional experiences. The user's emotional preferences, dislikes, and/or disinterests may be based, in part, on the user's emotional experience when viewing a particular media content event. Alternatively, or additionally, the user's emotional preferences, dislikes, and/or disinterests may be determined, in part, based on the user's real world life experiences that are associated with the user's emotions experienced during a real world event that they have personally experienced.

Then, embodiments of the user content preference identification system 100 identify one or more user content preferences, user content dislikes, and/or user content disinterests based on the user's emotional experiences that define their emotional preferences, dislikes, and/or disinterests. Based on the user content preferences, user content dislikes, and/or user content disinterests that are determined from the user's emotional preferences, dislikes, and/or disinterests, embodiments of the user content preference identification system 100 then identify one or more media content events that have one or more characteristics that are related to the cause of the user's emotional preferences, dislikes, and/or disinterests. Preferably, the identified media content events have not yet been consumed by the user (that is, the identified media content events have not yet been viewed by the user).

The identified media content events that may be of particular interest to the user (based on their determined emotional content preferences) that the user may wish to consume are then recommended to the user. Conversely, one or more of the identified media content events may be of little to no interest (based on their determined content disinterests), and/or may be disfavored or disliked by the user (based on their determined content dislikes). Here, recommendations may optionally identify media content events that are of little to no interest to, or even likely to be disliked by, the user. In some implementations, a combination of a plurality of different user content preferences, content dislikes, and/or content disinterests may be used to identify a particular recommended media content event.

The ESM 102 is configured to monitor biometrics of the user (who is wearing the ESM 102). The detected user biometrics indicate a current emotional state of the user. In an example embodiment, the ESM 102 includes an Electro-encephalography (EEG) sensor 108. EEG is an electrophysiological monitoring method to record electrical activity of the user's brain. The EEG sensor 108 is typically noninvasive, with one or more electrodes (not shown) placed along the inner surface of the ESM 102 so as to be in physical contact with the user's scalp. The EEG sensor 108 measures voltage fluctuations resulting from ionic current within the neurons of the brain. The detected ionic currents are indicative of the user's emotional state. Embodiments of the user content preference identification system 100 are able to identify event-related changes in the ionic current potentials based on a spectral analysis of the ionic current content of the EEG by analyzing, in the frequency domain, the type of neural oscillations (popularly called "brain waves") that are observed in EEG signals detected by the EEG sensor 108. Alternatively, or additionally, other types of biometric sensors may be used to detect the emotional state of the user.

The ESM 102 further includes at least one image capture device 110 that is oriented in an outward direction and in alignment with the user's eyes. The image capture device(s) 110 captures images that correspond to the visual field of view that is currently being seen by the user. Accordingly, embodiments of the user content preference identification system 100 are configured to obtain image information that can be used to identify one or more objects that are in the field of view of the user's current vision. Preferably, the image capture device 110 is operable to capture real-time video image data. Alternatively, the image capture device 110 may capture a series of still images (each separated by some duration).

In some embodiments, multiple image capture devices 110 may be used to provide a sufficiently large field of view for the analysis of the captured image information when objects that the user has seen are identified. Alternatively, or additionally, the additional image capture devices 110 may be used to capture images that are outside of the field of view of the user, such as behind the user, above the user, below the user, and/or to the sides of the user. Some embodiments may employ a 360° camera or the like. The use of a plurality of different image capture devices 110 oriented in differing directions enhances the ability of the user content preference identification system 100 to more accurately discern objects that may have elicited a currently detected emotional reaction from the user, particularly if the objects are not actually being viewed by the user.

The information from the EEG sensor 108 and the captured image information from the image capture device 110 each include time information that is used to synchronized the EEG sensor 108 information and the image capture device 110 information with each other. For example, a time stamp or the like may be used to identify a relative time of information acquisition by the EEG sensor 108 and the image capture device 110. The time information may optionally indicate real time. Accordingly, when the user experiences an emotional event (as indicated from an increased EEG activity level, for example), objects seen by the user at that same time, or just before a detectable change in the users' emotional state, may be identified from the captured image information provided by the image capture device 110. Then, an inference may be made by the user content preference identification system 100 that a particular object, when viewed by the user, is likely to elicit a particular emotional response from the user.

The ESM 102 may optionally include at least one microphone 112. The microphone(s) 112 detects sounds that are being heard by the user. Accordingly, embodiments of the user content preference identification system 100 can obtain audio information that can be used to identify one or more sounds in the immediate vicinity of the user that were heard by the user at that same time, or just before a detectable change in the users' emotional state. Some embodiments may have a plurality of microphones 112 to detect the sounds that are being heard by the user. Differences in sound detected at different ones of microphones 112 may be used to compute (triangulate) the location and/or direction of the source of the detected sound. In some embodiments, one or more of the microphones may be directional microphones that detect sound in a limited orientation from the microphone 112 so that the location and/or direction of the source of the detected sound.

The audio information from the microphone 112 may also include time information that is used to synchronized the EEG sensor 108 information and the image capture device 110 information with the audio information provided by the microphone 112. For example, a time stamp or the like may be used to identify a relative time of information acquisition by the microphone 112 (relative to the information provided by the EEG sensor 108 and the image capture device 110). The time information may optionally indicate real time. Accordingly, when the user experiences an emotional event (as indicated from an increased EEG activity level, for example), sounds heard by the user at that same time may be identified from the audio information provided by the microphone 112. Then, an inference may be made by the user content preference identification system 100 that a particular sound, when heard by the user, is likely to elicit a particular emotional response from the user.

At least one of the portals 104, such as the example portal 104a, is communicatively coupled to the ESM 102. Preferably, a portal 104 is communicatively coupled to the ESM 102 via a wireless signal 114, such as an infrared or radio frequency signal. Alternatively, or additionally, a wire-based connector may be used to communicatively couple a portal 104 to the ESM 102.

The receiving portal 104 is communicatively coupled to the user content preference identification system 100 via a suitable communication network 116. In some embodiments, a plurality of portals 104 are geographically distributed about a region of interest that the user is likely to be located in. The plurality of portals 104 increase the likelihood that the user's ESM 102 is communicatively coupled to at least one portal 104 at substantially all times. In some embodiments, when a plurality of portals 104 are concurrently receiving communications from the ESM 102, a selected one of the portals 104 communicated the received information to the user content preference identification device 106. If the user is moving, wherein a currently communicating portal 104 becomes out of range of the ESM 102, then communications can be handed off to another receiving ESM 102 (such communication hand off processes are well known in the arts). That is, the information provided by the ESM 102 can then be received by at least one portal 104 regardless of the user's current geographic location.

The information received from the ESM 102 may then be communicated from the portal 104 to the user content preference identification device 106 where an analysis of the user's emotional information is processed such that the user's emotional preferences, emotional dislikes, and/or emotional disinterest is determined. The portal 104 may be a special purpose device configured to communicatively couple to one or more ESMs 102. Alternatively, or additionally, the portal 104 may be a legacy mobile device (such as a smart phones, cellular phones, notebook computers, laptop computers, personal computers, wearable devices, or personal device assistants) a cell tower device of a cellular telephone system, an internet WiFi hot spot, a blue tooth receiver, or another suitable legacy device or system that enables the ESM 102 to communicate the user's emotional state information, captured image information, and/or detected audio information to the user content preference identification device 106.

In the various embodiments, the user content preference identification device 106 may concurrently be communicatively coupled to a plurality of different portals 104, and thus to a plurality of different ESMs 102. Accordingly, information from a plurality of ESMs 102 being worn by different users can concurrently provide information to the user content preference identification system 100 so that a the emotional state of a plurality of different users are monitored.

Summarizing, the ESM 102 continuously captures, in real time, information that is associated with, and that is indicative of, the user's current emotional state. Further, information pertaining to the user's life experience is captured by the ESM 102 as image information corresponding to what the user is seeing and/or audio information corresponding to sound that the user is hearing. The information associated with the user's emotional state and their life experience is communicated from the ESM 102 to the portal 104, and then to the user content preference identification system 100. This information is analyzed, and over time, the user content preference identification device 106 learns "why" a user may have an emotional preference, dislike, and/or disinterest about a life experience of a real world event and/or a viewed media content event.

The user content preference identification system 100 may then identify one or more emotional-based user content preferences, emotional-based user content dislikes, and/or emotional-based user content disinterests based upon anticipated emotional responses of the user if that media content event is consumed by the user. These identified emotional-based content preferences, dislikes, and/or disinterests are then used to identify one or more media content events that the user may be informed about. Preferably, the identified media content events have not yet been consumed (viewed) by the user. The identified media content events may then be indicated to the user as a recommended media content event (which may be a recommendation to view if some aspect of the media content event corresponds to a user's emotional preference, a recommendation to not view if some aspect of the media content event corresponds to a user's emotional dislike, or a recommendation to disregard if some aspect of the media content event corresponds to a user's emotional disinterest).

Preferably, the recommended media content events are communicated to an electronic media device 118 with a display. The recommended media content events can be visually indicated to the user on the display using any suitable textual format and/or other visual format. The display may be a component of, or communicatively coupled to, smart phones, cellular phones, notebook computers, laptop computers, personal computers, wearable devices, or personal device assistants. Alternatively, or additionally, the recommended media content events are communicated to an electronic media device 118 that is communicatively coupled to a media presentation system 120 with a display, wherein the recommended media content events can be indicated to the user on the display. The recommendations may be communicated to the media device 116 via the communication network 116.

In response to viewing the recommended media content events on the display, the user may choose to consume one or more of the recommended media content events. That is, the user may choose to view and/or record one or more of the recommended media content events (when at least one attribute of the recommended media content event corresponds to a user's emotional like). Alternatively, the user may choose to not consume one or more of the recommended media content events, particularly when the user content preference identification system 100 indicates to the user that they are likely to dislike the recommended media content events (when at least one attribute of the recommended media content event corresponds to a user's emotional dislike) and/or are likely to be disinterested in the recommended media content events (when at least one attribute of the recommended media content event corresponds to a user's emotional disinterest).

Further, embodiments of the user content preference identification system 100 may optionally indicate "why" the media content event has been recommended to the user. That is, supplemental information may be presented to the user that identifies or describes the previous and/or anticipated user emotional experiences that are related to characteristics of a particular recommended media content event. Thus, the supplemental information may assist the user in making a more informed decision when deciding if they wish to consume (view and/or record) or ignore the recommended media content event An example media device 118 may be a set top box that is configured to receive one or more media content streams 122 from a content provider. Other non-limiting examples of media devices 102 include smart phones, cellular phones, notebook computers, laptop computers, personal computers, wearable devices, or personal device assistants (PDAs).

In some instances, the media device 118 may be embodied with a portal 104. For example, the illustrated media device 118 includes the portal 104*b* that, when in proximity to the ESM 102, receives the emotional, image, and audio information being captured by the ESM 102. The media device 118 may then communicate the information received from the ESM 102 to the user content preference identification device 106 via the communication network 116. As another non-limiting example, smart phones, cellular phones, notebook computers, laptop computers, personal computers, wearable devices, or personal device assistants may be used as a portal 104.

The communication network 116 is illustrated as a generic communication system. In one embodiment, the communication network 116 comprises a cellular telephone system, such as a radio frequency (RF) wireless system. Accordingly, the media device 118, a portal 104, and/or the user content preference identification device 106 may each optionally include a suitable transceiver to enable wireless communications over the communication network 116. Alternatively, the communication network 116 may be a telephony system, the Internet, a Wi-fi system, a microwave communication system, a fiber optics system, an intranet system, a local access network (LAN) system, an Ethernet system, a cable system, a radio frequency system, a cellular system, an infrared system, a satellite system, or a hybrid system comprised of multiple types of communication media. Additionally, embodiments of the media device 118, a portal 104, and/or the user content preference identification device 106 may be implemented to communicate using other types of communication technologies, such as but not limited to, digital subscriber loop (DSL), X.25, Internet Protocol (IP), Ethernet, Integrated Services Digital Network (ISDN) and asynchronous transfer mode (ATM). Also, embodiments of the media device 118, a portal 104, and/or the user content preference identification device 106 may be configured to communicate over combination systems having a plurality of segments which employ different formats for each segment that employ different technologies on each segment.

Figure 2:
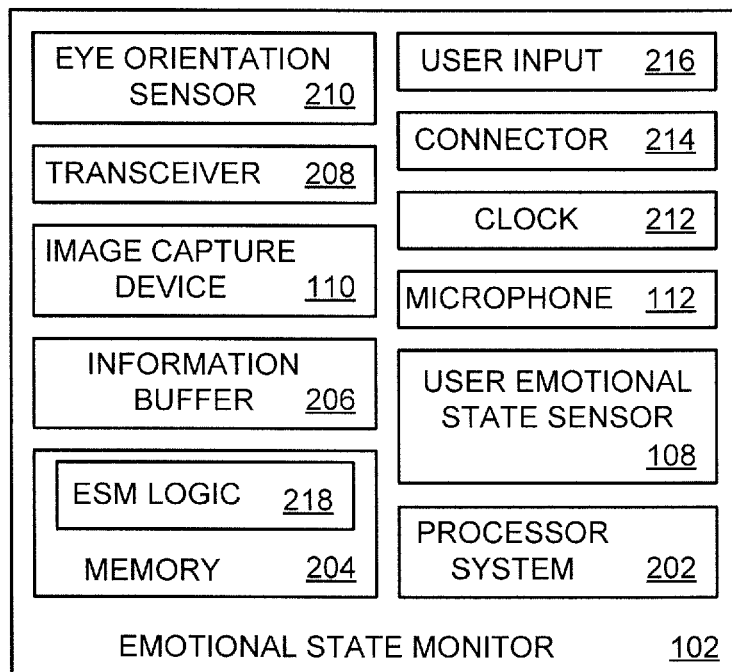
FIG. 2 is a block diagram of an embodiment of an emotional state monitor (ESM)

FIG. 2 is a block diagram of an embodiment of an exemplary ESM 102. The ESM 102 comprises a processor system 202, a user emotional state sensor 108, at least one image capture device 110, at least one microphone 112, a memory 204, an optional information buffer 206, an optional transceiver 208, an optional eye orientation sensor 210, an optional clock 212, and an optional connector 214. Other embodiments of the ESM 102 may include more components (not shown) and/or may include fewer components than those shown in FIG. 2.

Preferably, the components of the ESM 102 are enclosed in a structure or enclosure that is wearable by the user. In a non-limiting example embodiment, the ESM 102 resembles a pair of glasses that are worn on the head of the user. Another example may be a helmet-like device that encloses the user's head, such as a virtual reality head set, a head mounted display, or the like. Any suitable structure or enclosure for the components of the ESM 102, including multiple enclosures that contain different or common components, may be used by alternative embodiments of the user content preference identification system 100. The enclosure of the ESM 102 may optionally include other components, devices and/or systems that perform other tasks and functions that are not related to the user content preference identification system 100.

The EEG sensor 108 includes one or more sensors that are configured to detect brain wave activity of the user in real time. The detected brain wave activity is correlated to the emotional state of the user. For example, if the user enters into an excited state that corresponds to anticipation, surprise, joy, sadness, disgust, trust, anger, and/or fear, the brain wave activity information provided by the EEG sensor 108 can be analyzed to ascertain the particular state of the user's emotion (anticipation, surprise, joy, sadness, disgust, trust, anger, and/or fear) and the degree (amplitude) of the emotion on the part of the user. Supplemental information, such as an explicit input by the user, may be used to improve the determination of the particular emotional state of the user.

Other embodiments may alternatively, or additionally, use other types of biometric sensors that sense various characteristics of the user. Example biometric sensors may provide information that includes, but is not limited to, blood pressure information, heart rate information, body temperature information, and/or eye pupil dilation information. Any suitable biometric information that correlates to the emotional state of the user may be collected and analyzed by the various embodiments of the user content preference identification system 100. Such additional information may improve the accuracy and reliability of the determined user's emotional state.

Some embodiments of the ESM 102 include an eye orientation sensor 210. The eye orientation sensor 210 is an electronic device or system, such as a small image capture device, that is oriented towards at least one eye of the user who is wearing the ESM 102. The eye orientation sensor 210 provides eye orientation information that is used to determine the current orientation of the user's eye(s). The determined eye orientation can be used to better locate an object that the user is looking towards at any given instant in time. For example, if the user is looking to the left, then objects identified in the left hand side of the images captured by the image capture device(s) 110 are likely to be the particular object that the user was viewing. Similar to the time information used to coordinate the information provided by the EEG sensor 108, the image capture device(s) 110 and the microphone(s) 112, time information is also provided for the information acquired by the eye orientation sensor 210. Thus, determined eye orientation of the user can be synchronized with the information provided by the EEG sensor 108, the image capture device(s) 11, and the microphone(s) 112. The ESM logic 218 may optionally include any suitable eye orientation determination logic.

Timing information is used to synchronize the information received from the EEG sensor 108 with the image information received from the image capture device 110 and the audio information received from the microphone 112. The timing information may be provided by the clock 212. Alternatively, one or more of the EEG sensor 108, the image capture device 110, and/or the microphone 112 may have their own clock device that provides timing information. The time information provided by the clock 212 may be in real time. Alternatively, or additionally, the clock information provided by the clock 212 may be a relative indicator that indicates time relative to the information that is concurrently received from the image capture device(s) 110, the microphone(s) 112, the EEG sensor 108 and/or the eye orientation sensor 210.

Time information received from the clock 212 may be incorporated directly into the emotional state information received from the EEG sensor 108. The time information is used to identify the time of an identifiable emotional state of the user and/or the time that the user's emotional state has changed. Time information received from the clock 212 may also be directly incorporated into the captured image information that is received from the image capture device 110. The time information is used to identify the time of capture of portions of the video, and/or the time of capture of individual still images or image frames of a video. Alternatively, or additionally, time information received from the clock 212 may be directly incorporated into the audio information provided by the microphone 112. Accordingly, when the emotional state information, the captured image information, and the detected audio information is analyzed by embodiments of the user content preference identification system 100, the information can be synchronized together so that the real life experience of the user may be identified with a higher degree of accuracy and reliability.

Alternatively, the time information may be saved concurrently with corresponding portions of the received information from the image capture device(s) 110, the microphone(s) 112, the EEG sensor 108 and/or the eye orientation sensor 210. For example, a relational database approach may be used to define time bins or the like that concurrently stores received portions of the information from the image capture device(s) 110, the microphone(s) 112, the EEG sensor 108 and/or the eye orientation sensor 210, wherein the time information provided by the clock 212 identifies the time associated with the bin. Any suitable time correlation process may be used by the various embodiments so that the information received from the image capture device(s) 110, the microphone(s) 112, the EEG sensor 108 and/or the eye orientation sensor 210 can be synchronized together.

In some embodiments, the information buffer 206 receives and stores information from the image capture device(s) 110, the microphone(s) 112, the EEG sensor 108, the eye orientation sensor 210, and/or other biometric sensors. Here, the acquired information is temporarily stored (interchangeably referred to herein as being buffered or buffering) into the information buffer 206 for at least a predefined duration.

One skilled in the art appreciates that life events that affect the user's emotional state are likely to be experienced prior to the occurrence of a change in the user's emotional state. For example, if the user becomes frightened, "whatever life event" that caused the user to become frightened necessarily had to occur prior to the time that the user experienced their frightened emotional state. To illustrate, assume that a loud, brief and unexpected noise occurs in close proximity to the user. The user was most likely not in a frightened emotional state prior to the occurrence of the loud and brief noise. Further, at the precise instant in time of the occurrence of the loud and brief noise, the user was most likely not in a frightened emotional state. Only after the occurrence of the loud and brief noise does the user enter into the frightened emotional state because some duration of time is required for the user to audibly hear and discern the noise, and then react to their hearing of the noise. That is, the user becomes frightened only after hearing the loud and brief noise. This duration (time delay) between the occurrence of an event experienced by the user (visual, tactile and/or auditory) and the onset of a change in the user's emotional state is defined herein as a perception time delay.

Because of this inherent perception time delay in "whatever" life event that elicits an emotional state in the user, the information provided by the image capture device 110 and/or the microphone 112 must be available to the user content preference identification system 100 so that the cause of the user's emotional state can be determined. Accordingly, in embodiments that include the information buffer 206, information provided by the image capture device(s) 110, the microphone(s) 112, and/or the EEG sensor 108 are buffered (temporarily stored) into the information buffer 206. The stored information is retained for at least some predefined duration. Any suitable memory medium now known or later developed may be used to buffer the received information for some temporary duration.

In such embodiments that include the information buffer 206, the processor system 202 (executing the ESM logic 216 that has been retrieved from the memory 204) monitors the emotional information (the detected brain wave activity) received from the EEG sensor 108. When a significant change in the user's emotional state is detected (as indicated by a significant change in the detected brain wave activity of the user), the processor system notes the time of the occurrence of the change in the emotional state of the user. Then a duration of time can be defined that encompasses the time of the occurrence of the change in the emotional state of the user (a time before and a time after the time of the occurrence of the change in the emotional state of the user). This determined duration (defined by the determined before and after times) is used by the processor to retrieve a corresponding duration of buffered information from the EEG sensor 108, the image capture device(s) 110, the microphone(s) 112 that has been stored in the information buffer 206.

In some embodiments that omit the information buffer 206, the information from the image capture device(s) 110, the microphone(s) 112, and/or the EEG sensor 108 are communicated from the ESM 102 to the portal 104 in real time. The information is then communicated to the user content preference identification device 106. The received information is then buffered or is otherwise temporarily stored by the user content preference identification device 106. Alternatively, or additionally, the received information from the ESM 102 may be stored for a longer duration, and even stored permanently, in a persistent memory medium at the user content preference identification device 106 or at another suitable memory system or device.

The ESM 102 preferably includes a transceiver 208 that communicatively couples the ESM 102 with at least one portal 104. In the various embodiments, transceiver 208 is a communication device or system configured to receive and transmit radio frequency (RF) signals. It is appreciated that any suitable transceiver device or system may be used, and that the transceiver 208 may have a variety of components therein which are not described or illustrated herein for brevity. For example, but not limited to, the transceiver 208 may include as components a receiver and a transmitter device or system. Further, such components themselves may be separate devices or systems. Alternatively, or additionally, the ESM 102 may include a wire-based connector 214 that enables the ESM 102 to communicatively couple to a portal 104 using a wire type connector (not shown).

The ESM logic 218 includes communication logic that enables the ESM 102 to communicatively coupled to a plurality of different types of portals 104 using different communication formats via the transceiver 208 and/or the connector 214. In some situations, the user may select a particular portal 104 that the ESM 102 will be communicatively coupled to. For example, the ESM may be an augmented reality device that has been communicatively coupled to a media device 118 (having the portal 104b) via a view wire-based connector (using the connector 214), or via a wireless signal (using the transceiver 208). The ESM logic 218 may at other times enable the ESM 102 to wirelessly connect to a portal 104 that is configured to communicate over a cellular communication network 116. The ESM logic 218 may further include logic that automatically searches for one or more available portals 104, identify and select a preferred portal 104, and then establish a communication link 114 to that selected portal 104.

Figure 3:
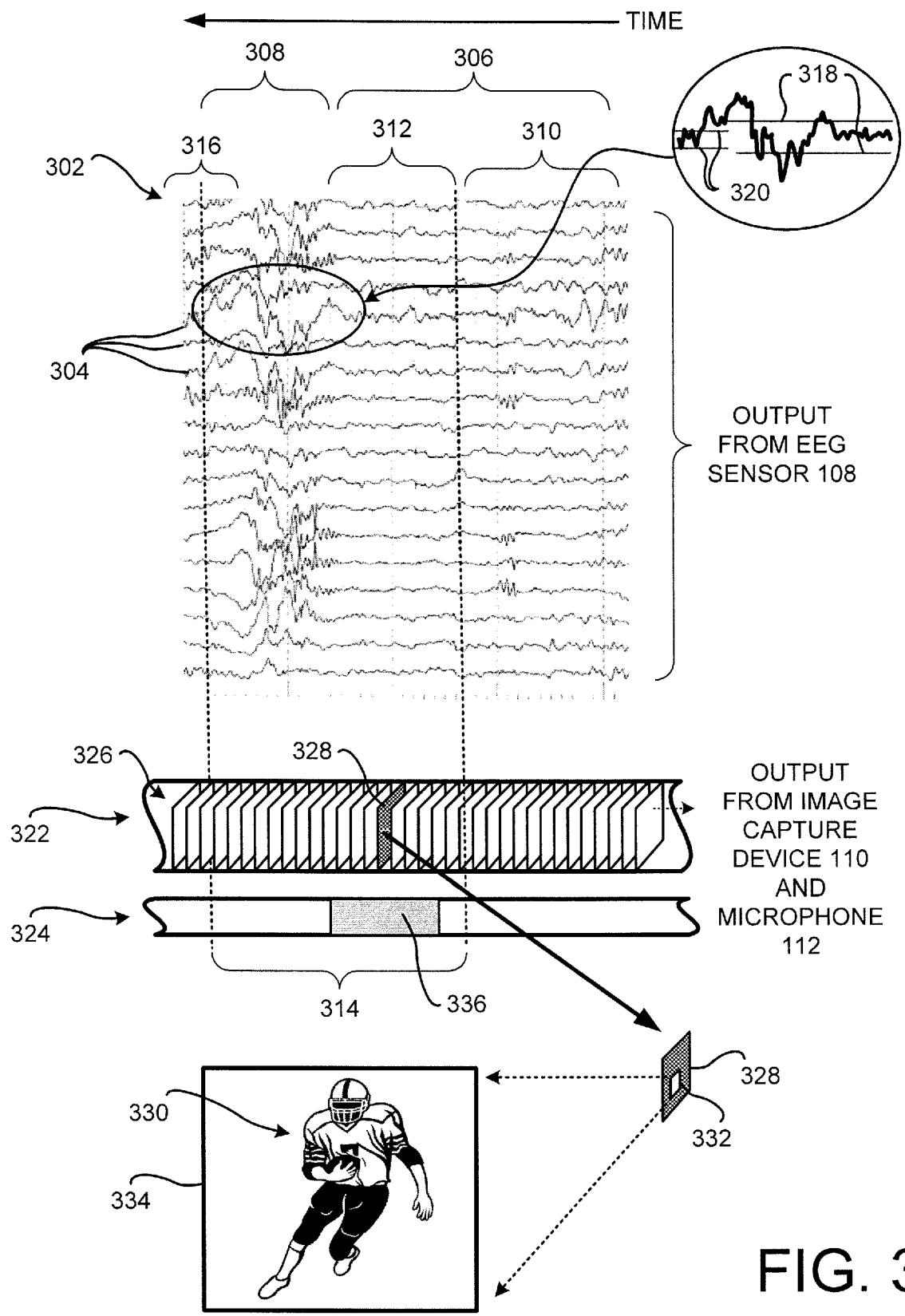
FIG. 3 is a hypothetical image of a duration of EEG information provided by an Electroencephalography (EEG) sensor.

FIG. 3 is a hypothetical image of a stream of EEG information 302 provided by the EEG sensor 108. Here, each of the brain wave lines 304 corresponds to an output of one of the sensors of the EEG sensor 108. Time is illustrated and is referenced from the earliest time being at the right hand side of the EEG information 302.

One skilled in the art appreciates that for the earlier first duration 306, the user was likely in a relatively relaxed and/or stable emotional state, as evidenced by the relatively flat brain wave lines 304 during that duration 306. During the later second duration 308, one skilled in the art appreciates that the user has likely transitioned into a relatively higher state of emotion, as evidenced by the relatively large and numerous spikes in the brain wave lines 304 during that duration 308 (interchangeably referred to herein as the emotional response duration 308).

Further, one skilled in the art appreciates that because of the inherent perception time delay corresponding to the time or duration required to realize the change of emotional state of a user after the occurrence of the life event (or stimulus) that cause the change in emotional state, that it is likely that during the duration 310, no particular event occurred that would initiate a change in the user's emotional state (since the change in emotional state is not apparent during the immediately following later duration 312). Rather, one skilled in the art appreciates that some particular life event initially started to occur during the duration 312 (interchangeably referred to herein as a life event occurrence duration 312) that initiated the change in the user's emotional state (as evidenced during the increased activity of the brain wave lines 304 occurring during the later duration 308). The life event occurring during the duration 312 may last any duration, and may or may not end prior to the detected change in the user's emotional state.

In the various embodiments, a duration 312 that immediately precedes an increase in activity of the brain wave lines 304 determinable for the duration 308 (that is associated with a change in the user's emotional state) is predefined. The predefined duration 312 is defined so that the initial occurrence of the life event is highly likely to have been initiated at some point in time within the duration 312. The predefined duration 312 may be specified by the operators of the user content preference identification system 100 during the initial configuration of the ESM 102, though the predefined duration 312 may be changed at any suitable later time. For example, a duration of ten seconds, thirty seconds, a minute, two minutes, several minutes or any other suitable predefined duration may be used for the predefined duration 312.

In response to identifying and/or detecting the initiation of a change in the user's emotional state (during the later occurring duration 308), the information previously acquired by the EEG sensor 108, the image capture device(s) 110, the microphone(s) 112, and/or the eye orientation sensor 210 (and the associated time, such as provided from the clock 212) begins to be accessed for detailed analysis. As described herein, the information was initially saved into the information buffer 206 and/or was streamed out to the user content preference identification device 106 as the information was being acquired.

The buffered information is saved until the brain wave activity lines 304 tend to show that the user is no longer experiencing a change in their emotions, such as at the end of the duration 308. At the end of the duration 308, the brain wave lines return to a relatively flat or stable level, as illustrated during the duration 316. The start of the duration immediately follows the end of the duration 308. In an example embodiment, the duration 308 may be a variable duration that is based on its start and concluding with the start of the duration 316. Alternatively, the duration 308 may be a predefined duration that is likely to have captured all of, or substantially all of, the user's emotional state change as indicated by the increased activity in the brain wave lines 304.

Here, embodiments of the user content preference identification system 100 will have saved information acquired from the EEG sensor 108, the image capture device(s) 110, the microphone(s) 112, and/or the eye orientation sensor 210 during the duration 314, interchangeably referred to herein as the life event duration 314. The duration 314 corresponds to the sum of the predefined duration 312 and the duration 308 characterized by the higher level of brain wave activity.

Accordingly, the information acquired by the EEG sensor 108, the image capture device(s) 110, the microphone(s) 112, and/or the eye orientation sensor 210 (and the associated time information, such as provided from the clock 212) is accessed from the start of the duration 312 to the end of the duration 308. That is, the information acquired during the duration 314 is accessed and then saved for detailed analysis.

A threshold-based system may be used by some embodiments to analyze the brain wave lines 304 to identify the onset (start) of an emotional state change and the end of an emotional state change. When the level of activity of a brain wave line 304 exceeds the value of an onset brain wave activity threshold 318, then embodiments of the user content preference identification system 100 determine that the onset of an emotional state change is occurring. In some embodiments, a predefined number of the plurality of brain wave lines 304 must exhibit an increase in the activity levels over the onset threshold value 318 before the user content preference identification system 100 determines that an onset of an emotional state change has occurred. Any suitable number of brain wave lines 304 may be defined to determine the onset of the emotional state change.

Depending upon the physical location of the particular EEG sensor that acquires information that generates a particular brain wave line 304, those particular brain wave lines 304 may be given a greater weighting factor and/or a lower onset threshold value 318 to indicate that these brain line waves 304 are more likely to be indicative of an onset of an emotional state of the user. For example, one skilled in the art understands that particular regions of the human brain are associated with different functions. Those regions of the human brain are known to be associated with emotions, and such regions may be relatively close to a particular EEG sensor (such that that particular EEG sensor picks up changes in brain activity in that region of the human brain). The information acquired by a sensor in close proximity to the area of the brain associated with emotions may be given more importance (via a greater weighting and/or a lower onset threshold 318) in the determination of a change (onset) in the emotional state of the user. In contrast, some regions of the human brain are known to be associated with motor functions (which, presumably, are not as relevant to emotions). Accordingly, information acquired by a sensor in close proximity to those areas of the brain that are associated with motor functions may be given less importance (via a lower weighting and/or a higher onset threshold 318) in the determination of a change in the emotional state of the user.

The end of the duration 308 (corresponding to an end in the change of the user's emotional state) may be similarly determined by another predefined threshold 320. When the value of movement in the brain wave lines 304 drops below the value of the threshold 320. Since after the end of the duration 308, the brain wave lines 304 (or at least tome predefined number of brain wave lines 304) have returned to a relatively flat or stable level that is less than the threshold 320, the end of the duration 308 is then identifiable by embodiments of the user content preference identification system 100. When determining the end of the emotional event, embodiments may use different weighting and/or thresholds 320 for particular ones of the brain wave lines 304.

One skilled in the art appreciates that the amount of data corresponding to the information acquired by the ESM 102 that has been stored in the information buffer 206 is ultimately limited by the storage capacity of the memory medium of the information buffer 206. At some point in time after the buffering of the acquired information into the information buffer 206, if no life event has been detected (based on an activity change in the brain wave lines 304), then the earlier acquired information may be overwritten, deleted, erased or otherwise discarded. For example, if no significant change in the brain wave lines 304 during the duration 308 is detected (indicating that the user's emotional state has not changed), at the conclusion of the duration 314, there is no need to further buffer or save the information (interchangeably referred to herein as stale data or stale information) for that duration 314.

Accordingly, embodiments of the ESM 102 are configured to receive a specification that defines a duration 316 that, in the event no significant activity of the brain wave lines 304 indicates a potential occurrence and/or onset of a change in the user's emotional state, the stale information for that duration 310 is overwritten with newer data, is erased, is deleted, or is otherwise discarded. In an example embodiment, the duration 316 is predefined based on a sum of the amount of time that is needed to reliably identify the onset of a change in the user's emotional state based on analysis of the activity of the brain wave lines 304 occurring during the duration 308. A margin of time may be added when defining the duration 316 to ensure that relevant information is not inadvertently overwritten, erased, deleted or discarded from the information buffer 206.

In an alternative embodiment, if no significant activity is detected in the brain wave lines 304 that indicates a potential occurrence and/or onset of a change in the user's emotional state, then the stale data corresponding to the end of the duration 308 (or data that has a time shortly after the end for the duration 310 by some predefined duration) is overwritten, is erased, is deleted or is otherwise discarded. The overwriting, erasing, deleting or discarding of old stale data may occur as new data is received from the ESM 102. For example, as a bit of new data is received from the ESM 102, the oldest corresponding bit of data may be overwritten, erased, deleted or discarded from the information buffer 206.

FIG. 3 also conceptually illustrates a stream of image information 318 captured by an image capture device 110 and a corresponding stream of audio information 320 acquired by a microphone 112 of the ESM 102. One skilled in the art appreciates that the illustrated streams of information are time-wise synchronized with each other and with the streams of the EEG information 302 having a plurality of brain wave lines 304 as described herein.

In response to determining the occurrence (onset) of a change in the user's emotional state (at the start of the duration 308), and the resultant determination of the start time and end time of the duration 314, embodiments of the user content preference identification system 100 pick out or otherwise access the portions of the streaming information associated with the duration 314. The accessed information is then saved for detailed analysis. The detailed analysis of the information acquired from the EEG sensor 108, the image capture device(s) 110, the microphone(s) 112, and/or the eye orientation sensor 210 (and the associated time, such as provided from the clock 212) during the duration 314 enables the user content preference identification system 100 to identify the cause (interchangeably referred to herein as the life event) that precipitated the change in the user's emotional state (as evidenced by the increased activity of the brain wave lines 304 during the duration 308).

Presumably, the life event which initiated the change in the user's emotional state occurred somewhere during the duration 314, and more particularly, during the duration 312. If the life event, at least in part, was the user viewing a particular object, then an image of the object will likely be included somewhere in the stream of image information 322 captured by at least one of the image capture devices 110 of the ESM 102. Alternatively, or additionally, any sounds heard by the user that may have initiated the change in the user's emotional state will have been recorded in the audio stream 324. In some situations, both objects seen by the user and sounds heard by the user may have precipitated the change in the user's emotional state. Accordingly, such objects and sounds may be identified from the information saved during the duration 314.

Summarizing, the information acquisition process associated with a change in the user's emotion state begins with the detection of an onset or occurrence of a change in activity levels of the brain wave lines 304 acquired by the EEG sensors 108. Then, the duration 314 is defined (as the sum of the duration 308 and the predefined duration 312). Next, the portions of the buffered or stored streams of information acquired by the EEG sensor 108, the image capture device(s) 110, the microphone(s) 112, and/or the eye orientation sensor 210 during the duration 312 are accessed and then saved for detailed analysis. The detailed analysis will result in the identification of viewed objects or heard sounds that likely initiated the change in the user's emotional state.

To conceptually illustrate how the user content preference identification system 100 may identify "why" the user's emotional state has changed (based on the identification of viewed objects or heard sounds that likely initiated the change in the user's emotional state), consider the hypothetical situation where the user's childhood friend has grown to become a notoriously well know and famous football player. One skilled in the art appreciates that when the user watches their friend make a game score, whether while watching their friend in person during a live game (referred to herein as a real life event or real life experience) or while watching their friend in a televised game (referred to herein as a content life event or a content life experience), the user will most likely feel a degree of increased emotional joy and/or satisfaction when their friend scores during the game. Here, this increased emotion of joy and/or satisfaction will be detectable from an analysis of the brain wave lines 304 acquired while the user is watching their friend's performance during the game.

At this juncture in the process performed by the user content preference identification system 100, it is assumed that there is no prior knowledge that the individual (here, the football player) is a close personal friend of the user. Embodiments of the user content preference identification system 100 will learn about the user's friend, will learn that the user experiences a higher degree of joy and satisfaction (user emotions) when watching their friend perform in a game, and will then construct an emotional statement with searchable keywords that include the identity of the friend. Using the searchable keywords in the emotional statement identifying the friend, embodiments will then search media content events to identify games where their friend may be seen, and then recommend the identified media content events to the user.

For example, once the identity of the friend is known, the friend may be a player in a televised college football game. Here, the emotional statement will include searchable keywords that include the friend's name and/or the team name that the friend is a member of Legacy prior art content recommendation systems based on user's viewing history would not be able to recommend the televised college game to the user because there will be no learned knowledge about the user's emotional experiences (such as learning that the user enjoys watching their friend perform in a game). Later, the player may become a professional football player. Embodiments of the user content preference identification system 100 will be able to identify televised games (based on the team names and/or player rosters for the named teams) where the user's friend is a player, and recommend the televised game to the user.

At some point, the user's friend may be a participant in and/or be the topic of a segment of a news cast program or a documentary program. Embodiments of the user content preference identification system 100 will be able to identify such news cast programs or documentary programs where the user's friend is a subject and/or participant (based on summary information describing topics and/or participants in the news cast programs or documentary programs), and recommend these media content events to the user.

As yet another example, the friend of the user may become an actor in a movie. Embodiments of the user content preference identification system 100 will be able to identify such a movie (based on summary information about the movie that includes the names of the actors in the movie) where the user's friend is an actor, and then recommend the movie to the user. Legacy prior art content recommendation systems based on user preferences determined from historical viewing patterns of the user would never be able to recommend such content to the user because there will be no learned knowledge about "why" the user may want to consume that content (because the experience an increased level of joy watching their friend).

Returning to FIG. 3, the stream of image information 322 is conceptually illustrated as a series of serially sequenced video image frames 326. Each video image frame 326 has image data or information that is used to render and present a particular image of the video captured by the image capture device 110. The video image frames 326 are serially presentable so as to create a moving picture (video).

To identify an object that may be associated with the change in the user's emotional state, interchangeably referred to herein as a candidate object, image frames 326 of the stream of image information 322 over the duration 314 are selected, picked or are other accessed so that the image data of the selected frame is analyzed to identify images of objects included in that selected image frame 328. Preferably, an image frame 328 that resides within the duration 312 is picked for analysis. The selected image frame 328 is analyzed using any suitable object recognition process or algorithm now known or later developed to identify objects shown in the selected image frame 328.

One skilled in the art appreciates that it is highly likely that a plurality of different objects will be identified from a selected image frame 328. Some of the identified objects will be candidate objects that may have caused the change in the user's emotional state. Other identified objects will likely not be associated with the change in the user's emotional state. Embodiments of the user content preference identification system 100 are configured to identify particular objects and their associated characteristics. Some of the identified objects may be known to potentially be the cause of the change in the user's emotional state. These particular objects may then be designated as candidate objects. Other identified objects may be known to not cause a change in the user's emotional state, and may then be disregarded for further analysis as to determining the actual source of the change in the user's emotional state.

Images of each identified candidate object, referred to herein as candidate object images, are then saved. Thus, each candidate object image is a smaller portion of the analyzed image frame. As a plurality of image frames 326 are selected and any physical objects in those image frames are identified, many of the identified objects from a series of selected image frames 326 will be of the same object. Other objects may be identified in only one of the image frames 326, or in a relatively few number of the image frames 326. One skilled in the art appreciates that since the orientation of the image capture device 110 that acquired the stream of image information 322 corresponds to the viewing direction of the user, that when a large number of image frames 326 each contain an image of a particular object (or plurality of identified objects), then it is highly likely that the user's attention was direct towards that particular object (or plurality of identified objects).

In view that multiple candidate objects may be identified from the image frames 326, the object images of the identified particular candidate object (or plurality of identified candidate objects) are saved for later presentation to the user. One or more representative candidate object images will be selected for presentation. The user will then be asked to identify which of the candidate objects were the source of their recollected change in emotional state. Further, the user may be asked to describe their changed emotional state. Alternatively, or additionally, the user may be presented the image frames 326 (as still images and/or as a video) and then asked to identify the objects that caused a change in their emotional state.

Returning to the hypothetical example of the user's personal close friend who is a football player, one skilled in the art understands that the stream of image information 322 was captured while the user was watching their friend playing in the game. Since the stream of image information was acquired by the image capture device 110 of the ESM 102, it is understood that the user would have been watching a live game or a televised game (a media content event). Regardless of what the user was viewing (the live game or the televised game), an image of their friend will be included in many of the image frames 326 that are within the duration 314.

For example, the video image frame 328 is selected and is used to generate the image that includes the image of the football player 330 who is the friend of the user. Here, a portion 332 (an area of space) of the image frame 328 has an image of the football player 330. The image data from the portion 332 is selected and an object image 334 that includes the football player 330 is generated there from, and is then saved as a candidate object image 332 by embodiments of the user content preference identification system 100.

At this juncture, one skilled in the art appreciates that the user content preference identification system 100 has not yet identified any particular identifiable objects as being the source of the change in the user's emotional state. Further, it is highly likely that a plurality of other object images will be generated of other identifiable objects that are visible in the analyzed image frames 326. For example, other players, referees, and/or bystanders may be identified. Structural objects, such a bleachers or goals, may be identified. Particular actions may also be identified from a series of analyzed image frames 326, such a game score or other important activity. However, at this juncture, embodiments of the user content preference identification system 100 require additional information to determine which of the particular identified objects are associated with the actual source that initiated the change in the user's emotional state.

In some embodiments, the information acquired from the eye orientation sensor 210 may facilitate identification of candidate objects that are likely sources of the change in the user's emotional state. The information about the orientation of the user's eyes may be used to define a particular region in the analyzed image frames 328 that the user's attention was directed towards. That is, the eye orientation sensor 210 may be used to identify a particular relevant area of an analyzed image frame 328. Objects that are identified which are outside of the identified area of the user's viewing direction may be disregarded as being candidate objects. Objects that are identified which are within the identified area of the user's viewing direction may be designated as being candidate objects Additionally, or alternatively, sounds in the audio information acquired by the microphone 112 is similarly analyzed to identify one or more sounds that were heard by the user. The identified sounds may also be the source of, or part of the source of, the change in the user's emotional state. Audio clips 336 containing the candidate sound are generated from the audio stream 324 acquired during the duration 314 and are saved as candidate audio sounds. However, at this juncture, embodiments of the user content preference identification system 100 require additional information to determine which of the particular identified sounds are associated with the actual source that initiated the change in the user's emotional state.

Further analysis of the brain wave lines 304 acquired by the EEG sensor 108 allow embodiments of the user content preference identification system 100 to identify particular emotional states of the user. More particularly, analysis of the frequency and phases of the neural oscillations of the plurality of brain wave lines 304 can provide an index of the dynamic interaction between brain regions involved in emotion perception. Any suitable methodology of analyzing EEG acquired information now known or later developed may be used by the various embodiments of the user content preference identification system 100 to identify particular emotions of the user.

In example embodiments, eight different emotions are identified from the acquired EEG information 302. The eight emotional states are anticipation, surprise, joy, sadness, disgust, trust, anger and fear. Further, the change in the user's emotional state may be viewed in terms of a range of emotions. Ranges of emotion include anticipation vs. surprise, joy vs. sadness, disgust vs. trust, and anger vs. fear. Although identification of other emotions is possible, these eight emotions are particularly useful is ultimately determining the user's emotional preferences, dislikes, and/or disinterests for content.

Anticipation is defined as an emotional feeling of excitement about some event that is going to happen, or is likely to happen, in the near future. Surprise is defined as an emotional feeling of wonder, astonishment, or amazement, as a result of experiencing an event that was unanticipated or that occurred unexpectedly. Joy is defined as an emotional feeling of emotion evoked by well-being, success, good fortune, or by the prospect of possessing what one desires. Sadness is defined as an emotional feeling characterized by feelings of disadvantage, loss, despair, grief, helplessness, disappointment and sorrow. Disgust is defined as an emotional feeling of revulsion or profound disapproval aroused by something unpleasant or offensive. Trust is defined as an emotional feeling that someone is good and honest and will not harm you, or that someone or something may be relied upon. Anger is defined as an emotional feeling characterized by a strong feeling of annoyance, displeasure, or hostility. Fear is defined as an emotional feeling of an unpleasant anticipation or awareness of danger, pain, and/or harm. Other embodiments may use fewer than the eight identified emotions, more than the eight identified emotions, and/or different emotions.

As time progresses, for a particular user, embodiments of the user content preference identification system 100 generate an emotional database that includes the acquired identified emotion events (where the emotional event is associated with one of the eight emotions: anticipation, surprise, joy, sadness, disgust, trust, anger and fear), identified candidate objects (and information to access stored candidate object images) and identified candidate sounds that may be the source of the change in the user's emotional state, and whether the acquired change in the user's emotional state occurred as a result of the user experiencing a real life event (interchangeably referred to herein as a real life experience), or, was the result of the user viewing a particular media content event (referred to herein as a content life experience or content life event). Further, magnitude or value information may be saved for each emotional event that is indicative of the degree of emotion that the user experience during the emotional event (as determined from the magnitude of change in the acquired brain wave lines 304). In an example embodiment, the emotional database may be visually presented to an observer using a matrix format (referred to herein as an emotion matrix).

For each emotional event, the information will include any associated emotions of anticipation, surprise, joy, sadness, disgust, trust, anger and/or fear. For each emotional event, at least one candidate object (and more likely a plurality of candidate objects) and/or a candidate sound (or a plurality of candidate sounds) will be associated with each emotional event. After a sufficient number of emotional events have been accumulated, embodiments may learn which objects and/or sounds are associated with particular emotions. That is, embodiments of the user content preference identification system 100 are able to correlate viewed objects and/or heard sounds with particular changes in emotional states.

Returning to the hypothetical example of the user's friend who has become a notorious football player, it is likely that over time the emotional database for the user will have a plurality of emotional events pertaining to the user's friend. Some life events, such as their friend scoring a game point or performing particularly well during a particular game play, may elicit an increase in the emotions of joy, anticipation, and/or surprise. Alternatively, if there is an accident that involves their friend, the user may experience an increase in anticipation, surprise, sadness, fear, and/or anger. Regardless of the change in emotional state of the user during the game, or over a series of games performed over time, embodiments of the user content preference identification system 100 will "learn" that the user's friend is associated with a change in the user's emotional state.

As noted herein, embodiments of the user content preference identification system 100 interact with the user at some point(s) in time to obtain user feedback regarding their particular experienced emotional states and to obtain an explanation of "why" the experienced their emotions. Embodiments will query the user about particular life events, ask them to recall the experience, identify their emotions that they were feeling during the life event, and then identify the viewed objects and/or heard sounds that precipitated their change in emotional state.

Returning to the hypothetical example of the user's friend who is a football player, embodiments of the user content preference identification system 100 will present to the user the candidate image objects identified from the captured images acquired by the image capture devices(s) 110, and/or present sounds acquired by the microphone(s) 112. The user will be asked to recall their emotional experience during the life event, and then identify one or more candidate objects and/or sounds that were the cause of the change in their emotional state. Here, the user would identify their friend shown in the candidate object images. Further, the user may be asked to identify the pertinent candidate object. Here, the user may say or provide suitable input that identifies the name of their friend.

Other candidate objects not associated with the change in the user's emotional state will be identified by the user as not being relevant to the change in their emotional state. These candidate objects can then be known to be objects that will not likely elicit an emotional change in the user.

Similarly, sounds may or may not precipitate and/or contribute to the change in the user's emotional state. In such cases, embodiments of the user content preference identification system 100 "learn" that some sounds are not likely to elicit an emotional response from the user. On the other hand, the recorded sounds presented to the user may cause the user to indicate that these sounds are associated with their change in emotions. For example, the playing of the user's national anthem or team song during the game may cause the user to experience the emotion of joy and/or satisfaction. The user may indicates such in response to a query from the user content preference identification system 100, and then the user content preference identification system 100 would "learn" that this particular music will likely elicit an emotional response from the user.

Alternatively, the user may have experienced no particular emotional change because of the playing of the national anthem and/or team song. Such indifference may be indicated by the user. (Rather, the user may have experienced an emotion caused by viewing their friend who was, coincidentally, viewed while the national anthem and/or team song was being played.) Thus, embodiments of the user content preference identification system 100 would "learn" that the user is likely indifferent to the playing of this particular music.

Once embodiments of the user content preference identification system 100 have identified a particular object and/or sound that is likely to elicit an emotion from the user, an emotional statement is defined. The emotional statement is a textual phrase that identifies the object and/or sound with particularity. That is, the emotional statement includes a textual description of the identified object(s) and/or sound(s) The emotional statement is associated with one or more emotions and/or may optionally include a textual characterization or description of the emotional state of the user. The emotional statement, in some embodiments, is referred to as a "whyse" statement. The term "whyse" is a combination of the two terms "why" and "wise" that indicates that the emotional statement is learned in an intelligent or wise manner that relates to why a user is likely to have an emotional response to a particular object and/or sound.

Figure 4:
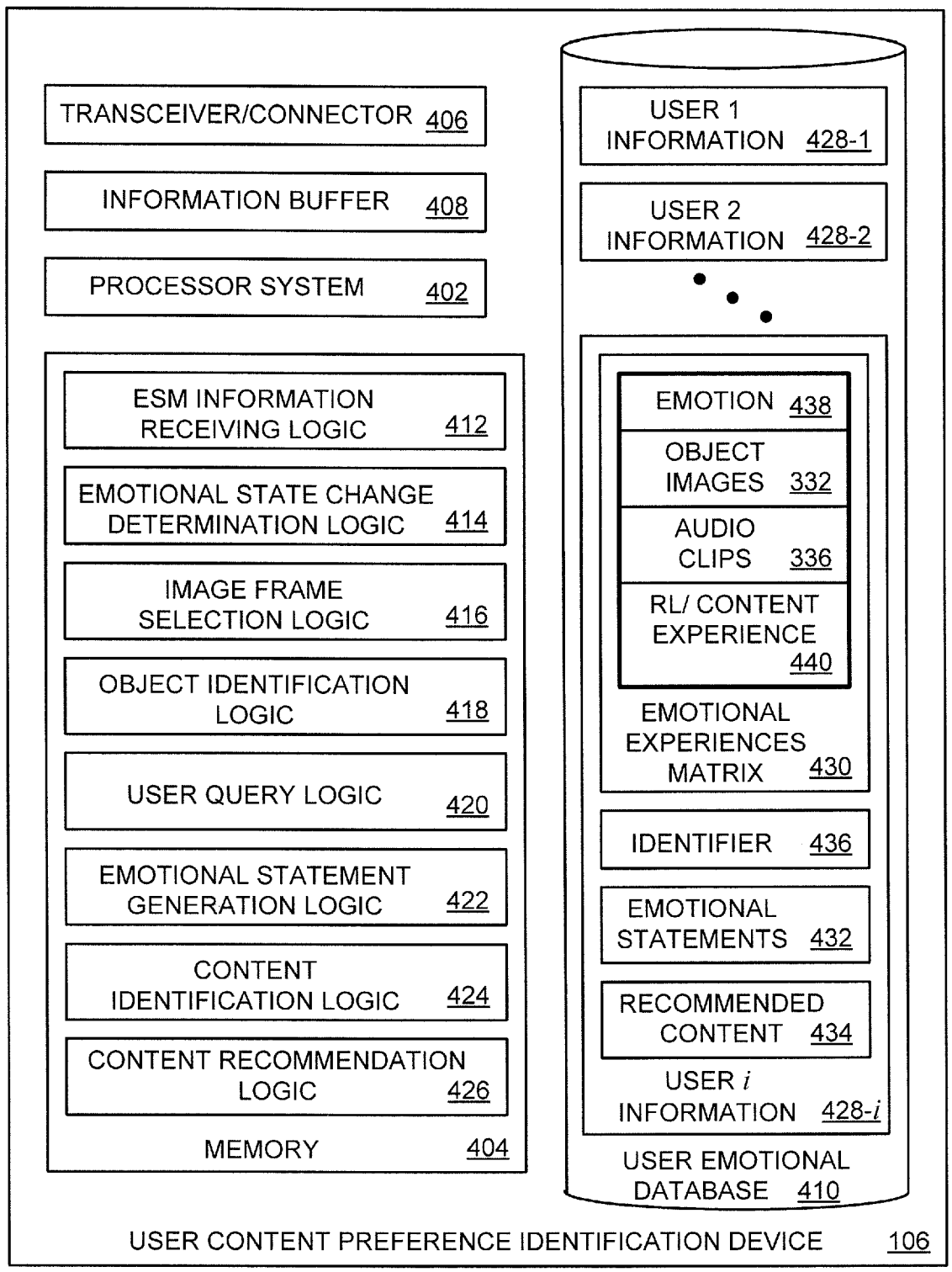
FIG. 4 is a block diagram of an example user content preference identification device.

FIG. 4 is a block diagram of an example user content preference identification device 106. The example user content preference identification device 106 comprises one or more processor systems 402, a memory 404, a transceiver/connector 406, an optional information buffer 408, and a user emotional database 410.

The memory 404 may be any suitable persistent memory medium or memory storage device that comprises regions for storing various logic modules. The logic modules, when executed by the processor system 402, perform the various functions and operations of the user content preference identification device 106. The logic modules include the emotional state monitor (ESM) information receiving logic 412, the emotional state change determination logic 414, the image frame selection logic 416, the object identification logic 418, the user query logic 420, the emotional statement generation logic 422, the content identification logic 424, and the content recommendation logic 426. Other logic modules (not described) may also reside in memory 404. The logic modules 412-426 are illustrated and described as separate logic modules in an example embodiment. However, the logic modules 412-426 may be integrated with each other, and/or may be integrated other logic modules that perform other functions. Further, one or more of the logic modules 412-426 may reside in separate memory mediums.

Additionally, one or more of the logic modules 412-426 may be concurrently executed by multiple processor systems 402.

The user emotional database 410 is a persistent memory medium that stores various information about each user. In example embodiments, the user emotional database 410 is implemented as a relational database using portions of the memory medium that have been uniquely associated with each individual user. For example, the user 1 information 428-1 is associated with a first user and the user information 428-2 is associated with a second user. It is appreciated by one skilled in the art that information for any number of user may be stored in the user emotional database 410.

The information contents for each user, such as for the exemplary $i^{th}$ user that has been stored in the user i information 428-$i$, includes the user's emotional experiences matrix 430, the user's emotional statements 432, recommended content 434, and a user identifier 436. The identifier 436 is any suitable identifier that uniquely identifies the user, such as a name, and address, an account number, or other suitable unique personal identifier.

The emotional experiences matrix 430 stores information for each life experience that is identified from the information provided by the ESM 102 being worn by the identified user. After a sufficient amount of time of monitoring a particular user, user information from a large number of life experiences for that particular user will be accumulated and will be stored in the emotional experiences matrix 430 for that user.

For each life experience for the identified user, the user's emotional experiences matrix 430 stores information identifying the particular emotion experienced by the user. The identified emotion (for example, but not limited to, anticipation, surprise, joy, sadness, disgust, trust, anger, and/or fear) is stored in the emotion 438 portion of the emotional experiences matrix 430. As noted herein, the user's particular emotion may be determined from an analysis of the user's brain waves 304 (FIG. 3) acquired from the ESM 102 (FIG. 1).

The RL/Content experience 440 is information that identifies whether the life experience occurred in real life (RL) or occurred while viewing (consuming) a media content event (denoted as a content life experience or a content life event). These emotional change events or experiences are generically referred to herein as life events or life experiences, respectively.

One or more object images 334 are generated from the analysis of the image information acquired by the image capture device(s) 110 of the ESM 102 for a particular real life event (a sub-type of a life event). As noted herein, the object images 334 are generated in response to determining that there has been a potential occurrence and/or onset of a change in the user's emotional state based on the analysis of the brain wave lines 304 during the duration 308. Generated object images 334 are stored in the user's emotional experiences matrix 430. Further, one or more audio clips 336 acquired by the microphone(s) 112 may be stored in the user's emotional experiences matrix 430 for the same real life event.

In some embodiments, the user emotional database 410 may employ a plurality of different memory mediums that store the user information for the plurality of different users. Such multiple memory mediums may be located locally at the user content preference identification device 106. Alternatively, or additionally, the multiple memory mediums may be distributed remotely from the user content preference identification device 106. In some embodiments, one or more remotely located memory mediums that store the user information of the user emotional database 410 may be configured to be communicatively coupled with a plurality of different user content preference identification devices 106. A working environment having the implemented user content preference identification system 100 is anticipated to have thousands, or even hundreds of thousands, of different users. Accordingly, a distributed emotional database 410 system and a plurality of user content preference identification devices 106 working in concert together would facilitate the processing of life event information received from a very large number of, or even an unlimited number of, different users.

The transceiver/connector 406 of the user content preference identification system 100 is a communication structure that communicatively couples the user content preference identification device 106 to the communication network 116. The transceiver/connector 406 may be configured to receive and transmit wireless communications via a wireless link established to the communication network 116. Alternatively, or additionally, the transceiver/connector 406 may employ a wire-based connection to become communicatively coupled to the communication network 116. Once the user content preference identification device 106 is communicatively coupled to the communication network, communication links can be established to a plurality of portals 104 that are receiving information acquired by one or more ESMs 102.

Embodiments may be provisioned with the optional information buffer 408. The information buffer 408 may operate similar to the information buffer 206 implemented in the ESM 102. Accordingly, a plurality of ESM(s) 102 that communicate on a real time basis, or on a near real time basis, the information acquired from the EEG sensor 108, the image capture device(s) 110, the microphone(s) 112, and/or the eye orientation sensor 210 (and the associated time, such as provided from the clock 212) is buffered into the information buffer 408. The processor system 402, executing the emotional state change determination logic 414, would monitor the received information on a real time basis, on a near real time basis, and/or at a later time, to identify the onset of an emotional state change in the user. Then, the information from the EEG sensor 108, the image capture device(s) 110, the microphone(s) 112, and/or the eye orientation sensor 210 (and the associated time, such as provided from the clock 212) for the duration 314 can be picked from the information buffer 408 for further processing.

The information buffer 408 may be a relatively large capacity type buffer memory device, and/or may be comprised of multiple buffer memory device units, to accommodate the information concurrently received from a relatively large number of different ESMs 102. In such operating environments, the information received from a particular ESM 102 includes identifying information that identifies that ESM 102 and/or the user who is wearing the ESM 102. Accordingly, the received information can ultimately be associated with a particular user.

In embodiments where the determination of an emotional state change is determined at an ESM 102 such that only the information acquired by the EEG sensor 108, the image capture device(s) 110, the microphone(s) 112, and/or the eye orientation sensor 210 (and the associated time, such as provided from the clock 212) during the duration 314 is communicated to the user content preference identification device 106, the information buffer 408 may be used to temporarily store the received information. Accordingly, the information may be retrieved from the information buffer 408 and be processed to add the information into that user's emotional experiences matrix 430.

The processor system 402, executing the ESM information receiving logic 412, processes the incoming information as it is being received from the plurality of ESMs 102. Accordingly, the processor system 402, executing the ESM information receiving logic 412, manages operation of the transceiver/connector 406 to manage communications to and from the communication network 116, operates to store received information into the information buffer 408, and then operates to access the stored information for further processing.

It is appreciated by one skilled in the art that the processor system 402 may be any suitable processor-based system or device. Further, some embodiments of the user content preference identification device 106 may employ multiple processor systems 402. The use of multiple processor systems would facilitate concurrent processing of information received from a plurality of different ESMs 102.

The processor system 402, executing the image frame selection logic 416, processes the image information for the duration 314 by selecting one or more image frames 326 (FIG. 3). Each selected image frame 326 is analyzed by the processor system 402 (executing the object identification logic 416) to identify one or more physical objects shown in the selected image frame 326. Depending upon the embodiment, the image frames 326 may be selected on a periodic basis over the duration 314. For example, every tenth image frame 326 (that is, image frames that are separated by nine intervening image frames 326) may be selected for analysis. Any suitable predefined number of intervening image frames may be used in the various embodiments.

Alternatively, image frames separated by a predefined separation duration may be selected. An example separation duration may be every two seconds. Any suitable predefined separation duration may be used in the various embodiments.

Some embodiments may be configured to use a first number of intervening frames or a first separation duration to initially identify one or more particular objects that are shown in each of the selected image frames 326. A single identifiable object(s) may be identified by the object recognition analysis of the selected image frames 326. For example, a single predominate object may be initially identified in the initially selected first plurality of image frames 326 that are analyzed in accordance with the object identification logic 416. The user content preference identification system 100 may then conclude with reasonable certainty that the identified object is most likely the candidate object (that precipitated the change in the user's emotional state). In such situations, additional image frames 302 may not need to be analyzed.

However, if no particular object(s) is identifiable in the analyzed first plurality of image frames 326, then more analysis may be required to identify any particular object(s) that is the likely source of the user's change in their emotional state. Accordingly, then an additional second plurality of intervening image frames 302 may be picked from the duration 314 for further analysis (based on a smaller number of intervening frames or based on a shorter second separation duration).

Conversely, a plurality of different objects may be initially identified in the selected first plurality of image frames 326. And, each image frame 326 of the first plurality may show different objects. Accordingly, the user content preference identification system 100 may not be able to identify candidate object with any degree of reliability or certainty. Accordingly, analysis of additional image frames 326 will be required to identify one or more candidate objects that may have precipitated the user's emotional state change. The additional second plurality of image frames 326 can then be selected and analyzed to identify the physical objects shown in the image frames 326.

Once candidate objects have been identified from the selected analyzed image frames 326, some embodiments are configured to generate object images 334 that are saved into the object images 334 portion of the emotional experiences matrix 430. Each object image (such as the exemplary object image 334) show the identified candidate object.

Alternatively, or additionally, a descriptor of the identified candidate object may be generated and saved (that includes a life event keyword). For example, a particular type of dog may be identified as a candidate object by the object identification logic 418. An image 334 of the dog and/or a descriptor identifying the type of dog may be saved into the object images 334. If multiple candidate objects are identified, then the multiple representative object images 334 (and any descriptors) are generated and then saved into the object images 334 portion of the emotional experiences matrix 430. Alternatively, the entirety of the image frame 326 that have the one or more identified candidate objects may be saved.

Object recognition algorithms are well known in the arts. Such object recognition algorithms, now known or later developed, may be used by embodiments of the user content preference identification system 100 to identify one or more candidate objects from selected image frames 326. Further, algorithms now known or later developed for selecting a portion of an image frame 326 having an identifiable object may be used to generate the object images 334.

When a plurality of image frames 326 are analyzed, and when the same object is identified in each image frame 326 (though the identified object likely is at a different portion or location in each analyzed image frame 326), the generated plurality of image objects 324 will be the same, substantially the same, or similar to each other. Accordingly, some embodiments are configured to save a single representative candidate object image 334 of the identified candidate object, or alternatively a limited number of candidate object images 334, into the emotional experiences matrix 430. Accordingly, embodiments of the user content preference identification system 100 may be configured to select a representative one of the generated object images 334 as a candidate object image 334. Alternatively, a selected number of the generated object images 334 may be saved into the user emotional database 410 so as to better represent the identified object. For example, a sufficient number of image objects (of the same physical object) may be generated and then stitched together to emulate a video clip of the object that the user saw during the associated life event.

The audio information is optionally analyzed during the duration 314 to identify sounds that may have, in whole or in part, precipitated the onset of the user's change in emotional state. If a candidate sound is identified, an audio clip 336 having the identified sound is generated and is stored in the audio clips 336 portion of the emotional experiences matrix 430. Candidate sounds may include songs, music, and/or other noise that is perceptible by the user.

Embodiments of the user content preference identification system 100 also ascertain if the user experienced a real life event or if the user was viewing a media content event during their change in emotional state. A flag, bit, or the like may be defined and stored into the RL/Content experience 440 portion of the emotional experiences matrix 430 to indicate a that the user's change in emotional state occurred during a real life event or a content event.

When the user is viewing and/or listening to a media content event, the image capture device(s) 110 and/or the microphone(s) 112 of the ESM 102, respectively, acquire image and sound information from the user's perspective. That is, the view of the content being seen by the user and the sounds of the audio track of the content being heard by the user are acquired.

One skilled in the art appreciates that if the life event is precipitated by consuming a media content event, that the particular media content event can be identified in a variety of manners. Once the particular media content event being consumed during the content life event is identified, then a wealth of information about that particular media content event is available that may be further analyzed to identify possible causes of the user's detected change in emotional state that was experienced while consuming that particular media content event.

Because the time that the user was consuming the media content event is known or is determinable based on time information from the ESM 102, embodiments of the user content preference identification device 106 may be optionally configured to identify the particular media content event that was being consumed by the user during that life experience. In an example embodiment, the user content preference identification device 106 accesses time of broadcast information (that may be available from an electronic program guide or the like) that corresponds to the time of the acquired information received from the ESM 102. Embodiments then identify available media content events that the user might have been consuming during the onset of the detected change in emotional state during the duration 314. Then, image and/or sound recognition logic may be able to identify the physical objects being seen and/or sounds heard by the user, and then compare the identified object and/or sound with images and/or sounds contained in a particular media content event.

For example, a particular song that has been identified in the sound being heard by the user (as acquired by the microphone(s) 112) may be included in the sound track of a media content event. Since information identifying the music and/or songs of the sound tracks used in a particular movie (which may be identified in meta data of the media content event and/or that may be stored at another remote site that stores information pertaining to media content events) is available to compare with the music and/or songs being heard by the user, the particular media content event being consumed by the user during the content life event may be identified.

Alternatively, or additionally, image analysis logic may identify an image(s) of one or more actors (physical objects) being viewed by the user (as acquired by the image capture device(s) 110). Then, facial recognition logic may process the image information to identify particular actors being viewed by the user. Information identifying the actors in a particular movie (which may be identified in meta data or at another remote site that stores information pertaining to media content events) is accessed by the user content preference identification device 106 to compare with the identified actors being seen by the user. When the identified actors seen by the user correspond to the actors of one of the plurality of media content events that are available for consumption by the user, then that particular media content event with the corresponding actors can be determined to be the media content event that was being consumed by the user during the content life event.

Alternatively, or additionally, the image information acquired by the image capture device(s) 110 may present image information in the vicinity of a display that the user is viewing the media content event on. For example, a digital indicator disposed on the surface of the a component of the presentation system 120 and/or the media device 118 may visually indicate the current channel that is being received by the media device 118 that the user is operating to present the media content event. Thus, identification of the visual digital display, and subsequent identification of the channel information, may be done by the user content preference identification device 106 based on analysis of image information acquired by the ESM 102. The channel information then is correlated with the information available from an electronic program guide or the like to identify the particular media content event being consumed by the user at the time of the content life event (since the channel identifier indicates that channel of broadcasting content).

Alternatively, or additionally, the media device 118 may be in communication with the ESM 102 and/or the portal 104. The media device 118 may be optionally configured to communicate identification information that identifies the currently presenting media content event and/or the currently received channel. For example the media device 118 may emit a wireless IR signal, a wirelesses RF signal, a Bluetooth signal or the like that is detectable by the ESM 102 and/or the portal 104. Then, the information identifying the media content event and/or the current channel can be provided to the user content preference identification device 106 for determination of the media content event being consumed by the user at the time of the potential occurrence and/or onset of a change in the user's emotional state.

Once the particular media content event has been identified, embodiments of the user content preference identification device 106 may access a variety of information pertaining to the identified media content event. For example, textual information describing the subject and/or theme of the identified media content event and/or a story line may be accessed (typically from a remote site that stores information pertaining to media content events). Actors of the identified media content event may be determined (potentially identifying actors that the user likes, dislikes, and/or is neutral about). Set location information may be acquired (potentially identifying locations that the user likes, dislikes, and/or is neutral about).

Based on time information provided by the ESM 102, individual scenes may be optionally identified. Then, scene information describing attributes of a particular scene may be obtained. For example, actors in that scene may be determined (potentially identifying actors that the user likes, dislikes, and/or is neutral about). Dialogue of that particular scene may be acquired (potentially identifying conversational topics that the user likes, dislikes, and/or is neutral about). Scene props (objects used to facilitate the filming of the media content event) may be identified (potentially identifying objects that the user likes, dislikes, and/or is neutral about). Scene sound track information may identify the songs and/or music being presented during that scene (potentially identifying songs or music that the user likes, dislikes, and/or is neutral about).

Summarizing, for each identified emotional event, embodiments of the user content preference identification system 100 identify the particular emotion(s) that the user experienced (stored in the emotion 438 portion of the user's emotional experiences matrix 430), identifies one or more candidate objects that may have precipitated the change in the user's emotional state (wherein object images and/or descriptors of the physical object are stored in the object images 334 portion of the user's emotional experiences matrix 430), identifies one or more sounds that that may have precipitated the change in the user's emotional state (stored in the audio clips 336 portion of the user's emotional experiences matrix 430), and determines if the user was experiencing a real life event or was viewing a media content event (stored in the RL/content experience 440 portion of the user's emotional experiences matrix 430). Accordingly, a record for each particular identified emotional life event can be generated and saved into the user emotional database 410. The database record would specify the emotion, include one or more candidate object images, optionally include one or more audio clips, and include a specification of the type of life event (a real life event or a viewing content event).

At this juncture, one skilled in the art appreciates that an additional level of analysis is required of the information stored in the user's emotional experiences matrix 430 before emotional statements can be determined. For example, for a particular life event, the object images 334 may include a plurality of object images for different identified physical objects seen in the analyzed image frames 326. Further, any identified sounds stored in the audio clips 336 may, or may not be, involved with the user's change in emotional state. There is no good way to automatically determine which of the particular objects, and/or whether any of the sounds heard by the user, are the source of the user's change in emotional state that occurred during the life event.

Accordingly, embodiments of the user content preference identification system 100 are configured to query the user about their life experience. An exemplary embodiment of the user content preference identification system 100, executing the user query logic 420, may query the user by first describing to the user one or more characteristics and/or attributes pertaining to the detected life event and the determined emotional state of the user (the determined user's emotion).

For example, the user may be shown the candidate object images generated during the duration 314. Candidate objects may be presented as still or video images on the media presentation system 120 and/or the media device 118 having a display. Alternatively, or additionally, candidate object images may be presented to the user via a suitable augmented reality device, such as the ESM 102 that resembles a pair of glasses that are worn on the head of the user. Another example may be a helmet-like device that encloses the user's head, such as a virtual reality head set, a head mounted display, or the like.

Sounds heard by the user at the time of the determined life event may be played back to the user. Sounds may be presented by the media presentation system 120 and/or the media device 118 having speakers or earphones. Alternatively, or additionally, candidate object images may be presented to the user via a suitable augmented reality device, such as the ESM 102 that resembles a pair of glasses that are worn on the head of the user. Another example may be a helmet-like device that encloses the user's head, such as a virtual reality head set, a head mounted display, or the like.

Other information may also be provided to the user. For example, if the user was consuming a media content event, information identifying the particular media content event and/or particular scene may be indicated to the user. The scene of the media content event that was being presented at the time of the potential occurrence and/or onset of a change in the user's emotional state may be optionally presented to the user.

The user, after contemplating the presented information, after viewing the acquired images and/or after hearing the acquired the acquired sounds, will be asked to identify any of the presented candidate objects that may have caused (precipitated) their emotional state change. The user may also be asked to identify any of the candidate sounds that may have caused their emotional state change. Additionally, the user will be asked to confirm whether the type of emotion they experienced during the life event is the same as the determined emotion, or whether their experienced emotion was different from the determined emotion (in which case the emotion information may be updated).

Optionally, if the user is wearing their ESM 102, acquired information may be analyzed while the user is being queried. For example, if a particular object or sound being presented to the user during the query again causes a change in the user's emotional state (as indicated by an increase in the acquired brain wave lines 304), then confirmation of the user's likely response to similar images and/or sound may be learned by embodiments of the user content preference identification system 100.

Further, when the user is being presented a plurality of candidate objects during a query, then the information acquired by the eye orientation sensor 210 may be used to identify the particular one(s) of the candidate objects that the user's view was directed to during the query. The user can then be presented the object(s) that they were looking at (as determined by the acquired eye sensor information). The user can then view the individual candidate object images one at a time, and their emotional response can be detected (as indicated by an increase in the activity of the acquired brain wave lines 304 during each presented identified sound).

Alternatively, the plurality of candidate objects may be presented one at a time in a serial fashion (using a suitable predefined delay), and the brain wave lines 304 may be analyzed to determine if the user is having an emotional response to a particular presented candidate object image. In one embodiment, rather than using a predefined duration for candidate object image presentation, the user's brain wave lines 304 can be monitored for an increased activity. If no increased activity in the acquired brain wave lines 304 is detected during presentation of a particular candidate object image, then the presented candidate image is not one that elicits an emotional response from the user. On the other hand, if an increased activity in the acquired brain wave lines 304 is detected during presentation of a particular candidate object image, then the presented candidate image can be identified as one that elicits an emotional response from the user.

In addition, or alternatively, an augmented reality avatar (interchangeably referred to herein as a "bot") may verbally ask the user specific questions during the query. For example, the bot may ask the user which particular candidate object(s) which caused their emotional state change. The bot may ask the user to describe their emotional response to view in the candidate object(s) (and/or to sounds). Natural language processing algorithms may then be used to convert the user's spoken answer to text, and then to identify the candidate object(s) that the user identified in response to the bot's verbal query.

Further, if a detectable emotional change is detected when the user is being presented an audio clip of candidate sounds, then the audio clip may be parsed into additional sections with specific identifiable sounds (thus increasing granularity of the audio information). The user can then hear the individual identified sounds one at a time, and their response can be detected (as indicated by an increase in the activity of the acquired brain wave lines 304 during each presented identified sound).

Summarizing, the user will be asked during the user query to specify their change in emotions and/or their emotional state during the life event (which occurred during the life event duration). The user's specified emotional state is compared to the determined emotional state that was determined from the information corresponding to the acquired plurality of brain wave lines acquired during the life event duration 314. The determined emotional state is correctly determined when the determined emotional state is the same as the user's specified emotional state. In contrast, the determined emotional state may be changed to the user's specified emotional state when the determined emotional state is different from the user's specified emotional state.

Optionally, other information and/or commentary provided by the user will be captured as part of the user query process. For example, the user may be asked to explain why they had a particular emotional response during that life event by the bot. For example, some cultural, religious, or other societal aspect of the user's life may be related to the particular emotional response of the user during the life event that is the subject of the user query. The user may also provide commentary about past experiences. For example, the user may have had a favorite puppy or other pet when they were young. If the identified object that is associated with the occurrence and/or onset of the change in the user's emotional state is a dog, and in view of the user's commentary regarding fondness for their childhood pet, embodiments of the user content preference identification system 100 may conclude that the user likes pet dogs (and accordingly, then identify media content events relating to and/or having story lines pertaining to pet dogs under the assumption that the user may like such media content events).

Based on the user's responses during the user query process, the candidate object(s) and/or candidate sound(s) that precipitated the change in the user's emotional state are identified by the user content preference identification system 100 based on the user's specification of which particular objects and/or sounds caused their emotional state change. These objects and sounds are indicated as being relevant to the user's change in emotional state, and are stored and are noted as being relevant to a user's emotion in the emotional experiences matrix 430 of the user emotional database 410 for that particular life event.

The other identified objects and/or sounds which were not identified by the user as being relevant to their emotional state change can then be identified as not being relevant to the user's emotional state change. In some embodiments, the information identifying non-relevant physical objects and/or sounds are stored or retained in the user's emotional experiences matrix 430 for that particular life event. These physical objects and/or sounds that the user did not indicate as being relevant to their changed emotional state may be flagged or otherwise identified as being physical objects and/or sounds that are of disinterest to the user. In some embodiments, these non-relevant objects and/or sound may be optionally deleted, erased or otherwise discarded.

In some instances, one or more of the identified objects and/or sounds may be identified by the user as being disliked by the user. In some embodiments, the information identifying such disliked physical objects and/or sounds are optionally stored or retained in the user's emotional experiences matrix 430 for that particular life event. These physical objects and/or sounds that the user indicated as being relevant to their changed emotional state may be flagged or otherwise identified as being physical objects and/or sounds that are disliked by the user. In some embodiments, these disliked objects and/or sound may be optionally deleted, erased or otherwise discarded.

In some situations, the user may not respond to a specific individual query. It may be that the user chooses not to respond because they have a great emotional reaction to the query (such as question from the bot, and/or a presented candidate object image or sound). Here, the user may otherwise experience great discomfort, anger, fear or other negative emotion such that they simply refuse to elaborate or articulate an answer to the specific query. Since the user is having an emotional response (as indicated by the currently acquired brain wave lines 304), embodiments of the user content preference identification system 100 may learn that that the user is experiencing a negative type emotion, and then conclude that particular query. That is, the user will not be asked related and/or follow up questions, and/or be presented related candidate object images and/or sounds.

Accordingly, after receiving user feedback obtained during the user query process, the user's emotional experiences matrix 430 will have, for a plurality of different life events, an accurate representation of the factors (what physical object the user saw and/or what sound the user heard) which precipitated the change in the user's emotional state. After similar information is obtained for the user from many life events, even thousands of or hundreds of thousands of live events, embodiments of the user content preference identification system 100 will have sufficient information to conclude (learn) what type of life events the user is likely to respond to, and be able to predict the emotional level and/or type of emotional response of the user to specific stimuli.

Furthermore, one skilled in the art appreciates that the information about what viewed physical objects and sounds heard by the user that are not relevant to the user's changed emotional state, and/or that are disliked by the user, may also provide relevant information about the user. For example, if a sufficient number of other life events also have similar, or even the same, identifiable objects and or sounds that are not relevant to the user's changed emotional state and/or are disliked by the user, then these objects and/or sounds may be associated with a disinterest or a dislike, respectively, on the part of the user.

For example, an identified sound may be that of an aircraft passing overhead. Some users may not have even recalled and/or noticed that an aircraft was in their vicinity during a plurality of different real life events. Thus, embodiments of the user content preference identification system 100, after a sufficient number of life events that recorded sounds of passing aircraft, may conclude (learn) that the user is not really interested in aircraft. In contrast, the user may have consistently become excited and/or joyful when they heard the sound of nearby passing aircraft. Thus, embodiments may conclude (learn) that the user has a particular like or preference for aircraft. Conversely, if the user became fearful each time they heard passing aircraft, embodiments may conclude (learn) that the user has a fear (dislike) of aircraft and/or has a fear of flying in general.

Based on one or more life experiences, one or more emotional statements 432 are generated and saved into the user's emotional experiences matrix 430. An emotional statement is a descriptive textual phrase that describes and/or characterizes the user's anticipated emotional response to perceived emotional stimuli (viewing a physical object and/or hearing a particular sound) during a future life event. That is, the emotional statement describes a predicted life event that is likely to generate a particular emotion experience(s) in the user if a similar life event occurs in the future. Preferably, the emotional statement describes "why" the user is likely to experience a particular emotional state. Preferably, the emotional statement identifies with particularity the object(s) and/or sound(s) that are anticipated to cause an emotional response when encountered by the user. The identification with particularity of the object(s) and/or sound(s) may be used to define searchable keywords that can be associated with the identified object(s) and/or sound(s).

The processor system 402, based on the information contained in the user's emotional experiences matrix 430 and while executing the emotional statement generation logic 422, generates one or more emotional statements. These generated emotional statements are then saved into the emotional statements 432 portion of the user information 428 of the user's emotional experiences matrix 430. For any individual user, over time, a plurality of different emotional statements may be generated as saved.

To generate an emotional statement, embodiments of the user content preference identification system 100 analyze the contents of the user's emotional experiences matrix 430 to identify a plurality of life experiences that had the same or similar emotional response in the user that were caused by the same or similar candidate objects and/or candidate sounds (as verified by the user during the user query process). Based on the plurality of identified common life experiences (that elicited in the user the same or similar emotions and that were caused by the same or similar viewed physical objects and/or heard sounds), embodiments of the user content preference identification system 100 determine and generate the emotional statement for the user. That is, embodiments conclude (learn) that a particular object viewed by the user at a future time, and/or that a particular sound heard by the user at a future time, can be expected to elicit a particular emotional response. Any suitable learning algorithm, such as an artificial intelligence algorithm, now known or later developed may be used by the various embodiments of the user content preference identification system 100.

For example, returning to the hypothetical user's friend who is a football player, an emotional statement such as, but not limited to, "the user enjoys watching their friend play in a game with the 'team,' act in a movie, or be a participant or topic of a news cast program or documentary" is generated (where the user has previously provided their friend's name, and the term "team" is the name of the particular sports team that their friend is a member of). The "why" portion of the example emotional statement is that the "user enjoys watching their friend." The anticipated life events are games, movies, news cast programs or documentaries (that their friend is a participant in). An alternative emotional statement may simply be the user "enjoys seeing their 'friend'." Emotional statements may be of any suitable length and/or complexity.

Here, embodiments have concluded (learned) that the user enjoys watching their close friend perform in a sporting event. During the user query process, the user presumably identified their friend (the candidate object) as being the cause of their emotional state change. Further, the user presumably identified their friend by stating their name. Since embodiments of the user content preference identification system 100 are configured to generate media content event recommendations based on learned user emotional experiences, embodiments may fairly conclude that if the named friend is an actor in a movie and/or is the subject or participant in a newscast event, then the user will most likely also like that type of content. Here, the friend's name and/or team name may be defined as a life event keyword that is used for searching for comparable or identical media content event keywords, wherein each of a plurality of media content events include at least one media content event keyword that describes a characteristic of the media content event.

Returning to the hypothetical example regarding aircraft, embodiments may generate an emotional statement that "the user is excited by aircraft" when the user consistently enjoys or becomes excited when hearing passing aircraft. The learned emotional statement may be further reinforced by other real life events wherein the user saw one or more aircraft, such as when the user has been at an airport, an air show, and/or an aircraft museum. Here, the terms aircraft, airport, flying, etc. may be defined as life event keywords that may be used for searching for comparable or identical media content event keywords of media content events to identify recommended media content events that the user may enjoy.

Conversely, embodiments may generate an emotional statement that "the user fears flying in aircraft" when the user consistently becomes fearful when hearing passing aircraft. This learned emotional statement may be further reinforced by other life events wherein the user saw one or more aircraft, such as when at the airport, an air show, and/or an aircraft museum, or even when the user has previously traveled in an aircraft. Further, the user's commentary provided during the user query process may have indicated a dislike for aircraft and/or flying. Here, the terms aircraft, airport, flying, etc. may be defined as life event keywords that may be used for searching for comparable or identical keywords of media content events to identify media content events that the user may want to avoid.

Summarizing, a plurality of emotional statements are generated for each user and are stored into the emotional statements 432 portion of the user's emotional experiences matrix 430. The emotional statements may span a wide range of emotions and a variety of stimuli (viewing a physical object and/or hearing a particular sound). Emotional statements contain one or more life event keywords. The emotional statement describes an attribute or characteristic of the physical object(s) the user saw and/or what sound(s) the user heard during the duration 308 corresponding to the potential occurrence and/or onset of a change in the user's emotional state. A life event keyword is a particular term or phrase of an emotional statement that is deemed to be particularly relevant to the user's changed emotional state. The life event keyword may be associated with a physical object seen by or a sound heard by the user during the life event. After a sufficiently long duration of monitoring a user wearing an ESM 102, hundreds or even thousands of different emotional statements and associated life event keywords may be generated and saved for each user.

One skilled in the arts appreciates that characteristics and/or attributes describing or pertaining to media content events are available from a variety of sources. Typically, information is available that includes textual information describing these various characteristics and/or attributes of the media content event. The textual information may define one or more media content event keywords that described the media content event. The descriptive information may include the title of the media content event, names of actors, producers, and other participants in the production of the media content event, identification of set locations, and other related information. Also, the information may include a description of the theme of the media content event and/or of individual scenes, interchangeably referred to herein as story elements and/or story lines. Example media content event keywords include, but are not limited to, actor names, names of other participants, names of set locations, or the like.

This textual descriptive information and/or media content event keywords may be created by the producers of the media content event. Alternatively, or additionally, the descriptive information and/or media content event keywords may be generated by operators of the user content preference identification system 100 and/or by other interested entities for use by embodiments of the user content preference identification system 100. Alternatively, or additionally, media content event keywords may be defined using an artificial intelligence system.

Other supplemental information may be associated with particular media content events. For example, some embodiments may include information describing audience reactions to the media content event and/or individual scenes. Community members of a social media group may have generated commentary (referred to herein as "dubs") describing their reaction to and/or view on the media content event and/or one or more particular scenes in the media content event. Media content event keywords may be generated based on this supplemental information.

After one or more emotional statements have been generated and stored, the processor system 402, executing the content identification logic 424, compares the life event keywords of the emotional statements with the media content event keywords for a plurality of different media content events. When the media content event keywords matches, or substantially matches, one or more of the life event keywords generated from an emotional statement of the user, that particular media content event may be identified as being of interest (or disinterest, or even dislike) to the user.

An emotional statement may generically describe a life experience, wish, or desire of the user. Such emotional statements may be referred to as "emotional dubs" herein. For example, during a user query process, the user may indicate that they always wanted to be an actor in a movie. The generated emotional dub, for example, might be the user has a "dream of being an actor." Story lines associated with media content event may be searched so as to identify media content events having themes and/or story lines about people who became actors (or people who tried, but failed, to become actors). Thus, the story line of the media content event would be the same, or substantially similar to, the user's emotional dub.

The identifiers of the candidate media content events are saved into the recommended content 434 portion of the user information 428 associated with that particular user. Other available information may be optionally stored. For example, many media content events have a brief statement describing the thematic content and/or subject of the media content event. This supplemental information may be stored with the identifier of the media content event.

Optionally, access information may be saved for each candidate media content event. The access information specifies how and/or when the media content event is or will be available for consumption by the user. For example, the access information may indicate that the media content event is scheduled for a broadcast on a particular channel at a specific future date and time. Alternatively, or additionally, the access information may indicate that the media content event is available from an on demand or pay for view type system, and optionally specify the access conditions that must be satisfied so that the user can access that media content event. Access information may indicate that the media content event is available for purchase on a memory medium (such as a compact disc, digital video disc, or the like) and/or for purchase in electronic form from a content provider.

Returning to the hypothetical user's friend who is a football player, a media content event (a football game) between two teams, one of which the user's friend is a member of, may be available for viewing (either immediately via on-demand or pay per view system, and/or during an upcoming broadcast). The football game may be identified when the life event keywords (the friend's name or the team name) match the media content event keywords (the names of players and/or teams participating in the media content event). Thus, embodiments may identify that particular media content event (the football game) as a candidate media content event.

As another non-limiting example, the user's friend may be an actor in a movie. Thus, the friend's name (a life event keyword) will match the names of the actors (media content event keywords) in the movie, and therefore identify the movie as being a candidate media content event. As yet another example, the user's friend may be the subject of a news cast or documentary. Here, the friend's name will match the names of individuals (media content event keywords) who are topics of and/or are participants in the news cast or documentary. Accordingly, embodiments identify these particular media content events (the news casts or documentaries) as candidate media content events.

Returning to the example of the user who enjoys or becomes excited by aircraft, media content events pertaining to aircraft (a media content event keyword) may be identified as candidate media content events because the term "aircraft" (a life event keyword) has been associated with the user based on a generated emotional statement for that user. Conversely, if the user fears aircraft and/or flying, media content events pertinent to aircraft and/or flying can be identified as being disfavored by the user.

After identification of candidate media content events for a particular user, embodiments of the user content preference identification system 100 will generate and communicate emotional-based media content event recommendations to the user. Here, the processor system 402, under the execution of the content recommendation logic 426, generates an emotional-based content recommendation list that is communicated to a user device. The recommended media content event may be indicated to the user as a media content event that the user is likely to enjoy in response to determining that the emotional state of the user is anticipation, joy, trust or another emotion that the user is likely to enjoy when consuming the recommended media content event. The recommended media content event may be indicated to the user as a media content event that the user is likely to dislike in response to determining that the emotional state of the user is sadness, disgust, anger, fear that the user is likely to dislike when consuming the recommended media content event. The recommended media content event may be indicated to the user as a media content event that the user is likely to be disinterested in when determining that the emotional state of the user is not one of anticipation, joy, trust, sadness, disgust, anger, fear or other strongly felt emotion that the user is likely to experience when consuming the recommended media content event. That is, a recommendation may be for media content event likes, dislikes and/or disinterests based on the determined likely user emotional response when consuming the media content event.

The emotional-based content recommendation list presents at least a listing of recommended candidate media content events that have been recommended for consumption by the user. Other supplemental information, such as supplemental information available from an electronic program guide (EPG) or the like, may also be included in the emotional-based content recommendation list.

Preferably, the emotional-based content recommendation list is graphically presented on a display of the user's device. Any suitable format for an emotional-based content recommendation list may be used by the various embodiments. Further, the emotional-based content recommendation list may be presented using an interactive format wherein the user may schedule a particular one of the recommended media content events for recording and/or for immediate presentation. Some emotional-based content recommendation lists will allow the user to set a reminder to view the media content event at a later time and/or at a particular location and/or particular user device. For example, the user may interactively make a selection of a particular recommended media content event using their cell phone or smart phone, and then set a reminder to watch the selected media content event at their home using their home media device (which may be a set top box or the like). The user may even select the media content event for recording by their home media device 118 when the media content event is broadcast at a future date and time indicated in electronic program guide (EPG) information.

Embodiments may even indicate on the emotional-based content recommendation list particular media content events that are expected to be disfavored by the user. For example, if the user has a fear of aircraft or flying, then media content events associated with aircraft and/or flying may be indicated to the user because embodiments of the user content preference identification system 100 has learned that the user does not like to experience the particular emotion associated with that object and/or sound. Accordingly, the user appreciates that they may not want to watch and/or record such aircraft-related media content events.

As another example, a particular actor may not be of particular interest to the user. If a media content event with that actor is scheduled for a broadcast at a date and time where the user typically views content, the notification to the user may provide the opportunity for the user to do something else or seek alternative content (e.g., rent a DVD movie or the like for home viewing during that date and time).

Summarizing, the life event keywords derived from the user's emotional statements are compared with media content event keywords for available media content events. Once a match between one or more life event keywords and media content event keywords is found, the identified media content events are identified as candidate media content events. That is, candidate media content events are identified that are likely to elicit a change in the user's emotional state that is the same as, or is similar to, the life events that caused a change in the user's emotional state. The candidate media content events are then used to generate an emotional-based content recommendation list that identifies the candidate media content events. Optionally, the emotional-based content recommendation list provides access information to the user describing how and when to access each recommended candidate media content event. Alternatively, or additionally, the emotional-based content recommendation list may interactively permit the user to immediately access a media content event, schedule a media content event for recording, and/or set a viewing reminder for the media content event.

In an example embodiment, the information in the emotional-based content recommendation list may be integrated into an EPG. When the user views the EPG while consuming content, the EPG may indicate recommend media content events that are likely to be of interest (liked or favored) to the user, may indicate disfavored media content events that are likely to be disliked by the user, and/or media content events that are likely to be of no interest (disinterest) to the user. Suitable icons or other graphical artifacts may be added to a presented EPG to indicate an emotional-based content recommendation. For example, a smiley face icon may be used to indicate a suggested media content event that the user is likely to enjoy, and an unhappy face icon may be sued to indicate a media content event that the user is likely to dislike.

In summary, the like, dislike and/or disinterest content recommendations are based on an anticipated emotional response that is anticipated be experienced by the user if the user consumes that particular media content event. Such emotional-based content recommendations are in contrast to legacy content recommendation systems that identify media content recommendations based on historical user viewing patterns.

Figure 5:
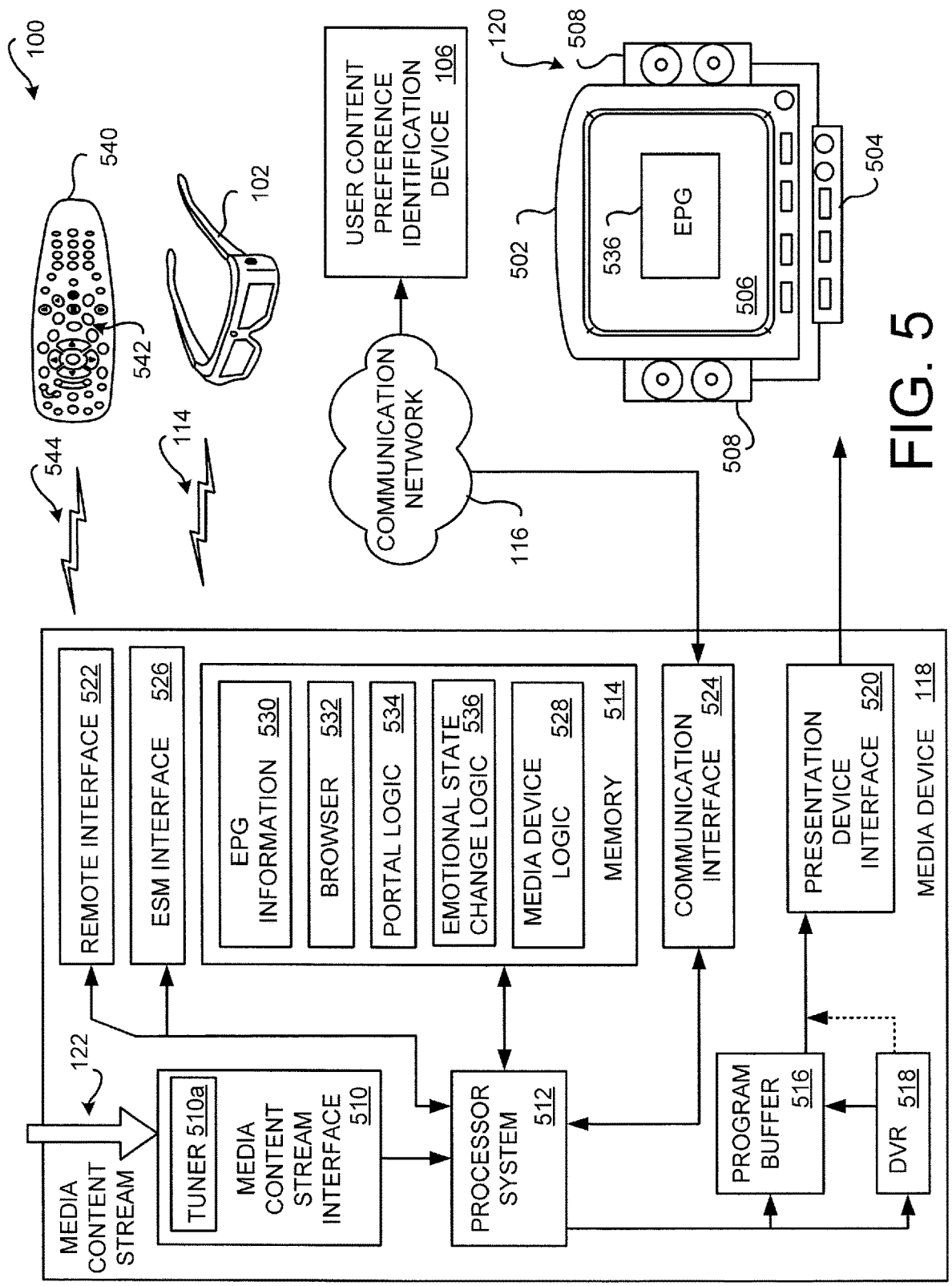
FIG. 5 is a block diagram of an embodiment of the user content preference identification system that is operable to control a media device.

FIG. 5 is a block diagram of an embodiment of the user content preference identification system 100 that is operable to control a media device 118, such as, but not limited to, a set top box (STB). Embodiments of the user content preference identification system 100 may be implemented in other media devices, such as, but not limited to, stereos, surround-sound receivers, radios, televisions (TVs), digital video disc (DVD) players, digital video recorders (DVRs), cellular phones equipped with video functionality, personal device assistants (PDAs), game playing devices, or personal computers (PCs) that are configured to present a video-based media content event that is received in a media content stream 122.

The exemplary media device 118 is communicatively coupled to a media presentation system 120 that includes a visual display device 502, such as a television (hereafter, generically a TV), and an audio presentation device 504, such as a surround sound receiver controlling an audio reproduction device. The video portion of a currently presenting media content event is presented to the user on a display 506 of the visual presentation device 502. The audio portion of the media content is reproduced as audible sounds by one or more speakers 508 of the audio presentation device 504. Other types of output devices may also be coupled to the media device 118, including those providing any sort of stimuli sensible by a human being, such as temperature, vibration and the like. In some embodiments, the media device 118 and one or more of the components of the media presentation system 120 may be integrated into a single electronic device.

The non-limiting exemplary media device 118 comprises a media content stream interface 510, a processor system 512, a memory 514, a program buffer 516, an optional digital video recorder (DVR) 518, a presentation device interface 520, a remote interface 522, a communication interface 524, and an optional ESM interface 526. The memory 514 comprises portions for storing the media device logic 528, the electronic program guide (EPG) information 530, an optional browser 532, the portal logic 534, and the emotional state change logic 536. In some embodiments, the media device logic 528, the portal logic 534, and the emotional state change logic 536 may be integrated together, and/or may be integrated with other logic. In other embodiments, some or all of these memory and other data manipulation functions may be provided by using a remote server or other electronic devices suitably connected via the Internet or otherwise to a client device. Other media devices may include some, or may omit some, of the above-described media processing components. Further, additional components not described herein may be included in alternative embodiments.

The functionality of the media device 118, here a set top box, is now broadly described. In a satellite broadcast system, a media content provider provides media content that is received in one or more multiple media content streams 122 multiplexed together in one or more transport channels. The transport channels with the media content streams 122 are communicated to the media device 118 from a media system sourced from a remote head end facility (not shown) operated by the media content provider. The media device 118 is configured to receive one or more broadcasted satellite signals detected by an antenna (not shown). Non-limiting examples of other media systems that broadcast a media content stream 122 include a cable system, a radio frequency (RF) communication system, and the Internet. Here, broadcasting refers to the process of communicating one or more media content streams 122 over a broadcast communication system (not shown) to a plurality of media devices 118 that are communicatively coupled to the broadcast communication system. Often, the media content is broadcast to hundreds or, or even thousands of, media devices 102 that concurrently receive the broadcasting media content stream(s) 122.

The one or more media content streams 122 are received by the media content stream interface 510. One or more tuners 510a in the media content stream interface 510 selectively tune to one of the media content streams 122 in accordance with instructions received from the processor system 512. The processor system 512, executing the media device logic 528 and based upon a request for a media content event of interest specified by a user, parses out media content associated with the media content event of interest. The media content event of interest is then assembled into a stream of video and/or audio information which may be stored by the program buffer 516 such that the media content can be streamed out to components of the media presentation system 120, such as the visual display device 502 and/or the audio presentation device 504, via the presentation device interface 520. Alternatively, or additionally, the parsed out media content may be saved into the DVR 518 for later presentation. The DVR 518 may be directly provided in, locally connected to, or remotely connected to, the media device 118. In alternative embodiments, the media content streams 122 may stored for later decompression, processing and/or decryption.

From time to time, information populating the EPG information 530 portion of the memory 514 is communicated to the media device 118, via the media content stream 122 or via another suitable media. The EPG information 530 portion of the memory 514 stores the information pertaining to the scheduled programming of available media content events. The information may include, but is not limited to, a scheduled presentation start and/or end time, a program channel, and descriptive information. The program's descriptive information may include the title of the program, names of performers or actors, date of creation, and a summary describing the nature of the program. Any suitable information may be included in the program's supplemental information. The information may include one or more media content event keywords, and/or may be sued to determine media content event keywords. Upon receipt of a command from the user requesting presentation of an EPG display, the information in the EPG information 530 is retrieved, formatted, and then presented on the display 506 as an EPG 538.

The exemplary media device 118 is configured to receive commands from a user via a remote control 540. The remote control 540 includes one or more controllers 542 disposed on the surface of the remote control 540. The user, by actuating one or more of the controllers 542, causes the remote control 540 to generate and transmit commands, via a wireless signal 544, to the media device 118. Preferably, each individual one of the controllers 542 has a specific predefined function that causes a specific operation by the media device 118 and/or by components of the media presentation system 120. The commands communicated from the remote control 540 then control the media device 118 and/or control components of the media presentation system 120. The wireless signal 544 may be an infrared (IR) signal or a radio frequency (RF) signal that is detectable by the remote interface 522.

The processes performed by the media device 118 relating to the processing of the received media content stream 122 and communication of a presentable media content event to the components of the media presentation system 106 are generally implemented by the processor system 52 while executing the media device logic 528. Thus, the media device 118 may perform a variety of functions related to the processing and presentation of one or more media content events received in the media content stream 122.

The portal logic 534, when executed by the processor system 512, is configured to receive the information acquired by the ESM 102, preferably via the wireless signal 114, at the ESM interface 526. Alternatively, the information from the ESM 102 may be received via a wire-based connector at the ESM interface 526. The portal logic 534 is further configured to communicate information from the media device 118 to the user content preference identification device 106, via the communication network 116 that is communicatively coupled to the media device 118 via the communication interface 524. Accordingly, the non-limiting example media device is operable as a portal 104a (FIG. 1).

The emotional state change logic 536, when executed by the processor system 512, is configured to perform a variety of operations pertaining to functions of the user content preference identification system 100. The emotional state change logic 534 may include one or more of the operations and/or functions performed by the emotional state monitor (ESM) information receiving logic 412, the emotional state change determination logic 414, the image frame selection logic 416, the object identification logic 418, the user query logic 420, the emotional statement generation logic 422, the content identification logic 424, and/or the content recommendation logic 426 implemented in the user content preference identification device 106 (FIG. 4). Accordingly, detailed description of the such functions of the emotional state change logic 534 are not described in detail since such functions are described in relation to the operation and functionality of the user content preference identification device 106.

The exemplary media device 532 includes an optional browser configured to communicatively couple the media device 118 to a remote site (not shown) and to access supplemental information pertaining to media content events and/or to remotely stored EPG information. In some embodiments, when the emotional-based content recommendation list is generated and is presented on the display 506 to the user, the emotional state change logic 536 can access the media content event supplemental information for incorporation into the emotional-based content recommendation list. Alternatively, or additionally, when the EPG 536 is generated and then presented on the display 506, information pertaining to the recommendations of the emotional-based content recommendation list may be integrated into the presented EPG 536.

In some embodiments, the media device receives a continuous stream of information acquired by the ESM 102. In such embodiments, the emotional state change logic 534 monitors the brain wave lines 304 to detect a potential occurrence and/or onset of a change in the user's emotional state. The received information from the ESM 102 has been stored into the program buffer 516, into another dedicated buffer memory device (not shown), or into another suitable memory medium. Then, the information acquired during the duration 314 may be optionally communicated from the media device 118 to the user content preference identification device 106. The emotional-based content recommendation list from the user content preference identification device 106 for the particular user of the media device 112 may be returned to the media device 112.

In some embodiments, a plurality of different users are associated with a particular media device 112. Accordingly, since each of the different users are separately providing input information from their personal ESMs 102, individual or unique emotional-based content recommendation lists can be generated for reach individual user. In practice, the media device receives identifying information that identifies each particular user, and can then present the corresponding information in the emotional-based content recommendation list for that particular identified user. Some media devices 112 may be configured to automatically identify particular users.

If a plurality of users are present, some embodiments may be configured to combine the individual emotional-based content recommendation list for each user into a composite emotional-based content recommendation list that indicates recommendations of the plurality of users. Media content events that are commonly liked, disliked, or of disinterest to the plurality of user's may be presented in a composite emotional-based content recommendation list. Here, only media content events that are liked by all of the present users, disliked by all of the present users, and/or are on no interest to the present users are incorporated into the composite emotional-based content recommendation list. An example embodiment simply compares the media content events identified in the individual emotional-based content recommendation lists for each present user, and when a match is found for particular media content events, those matching media content events are incorporated into the presented composite emotional-based content recommendation list.

In some embodiments, all media content event recommendations are indicated to the plurality of users in the composite emotional-based content recommendation list. The user's name or other identifier is included in the presented composite emotional-based content recommendation list so that each different user can identify particular media content event recommendations that are directed to their emotional characteristics. Alternatively, or additionally, a color scheme may be used to provide color-based textual information or backgrounds identifying the recommended media content events, wherein a particular text color and/or background color is associated with a particular user.

The emotional experiences of the user may be used for other purposes in addition to generating an emotional-based content recommendation list. In a social community environment, a plurality of users with common and/or similar experiences may be identified. For example, a plurality of users who enjoy aircraft may be identified. Here, a plurality of users may be identified in the community that have emotional statement with the same or similar keywords and the same or similar anticipated emotional responses. A social community environment platform (the program and system that manages the social community) supporting the community members may then communicate user identification information to those identified users (community members) who have common and/or similar experiences that are likely to result in common and/or similar emotions. The social community environment platform may then introduce these users having a common emotional characteristic or interest to each other, and optionally facilitate the formation of a community of like-minded users.

Additionally, or alternatively, the emotional state information used to identify media content recommendations that have common and/or similar experiences may be shared by the social community environment platform with the identified like-minded user's. That is, if for example a community of aircraft enthusiasts has been created on the social community environment platform, and if a new media content event pertaining to aircraft becomes available, then all of the user's who are members of this community can be advised, through a recommendation, of the availability of the new media content event.

Some alternative embodiments may locally store some or all of the user information 428 locally in the user's media device 118 and/or in another electronic device of the user in the memory 514 or in another suitable memory medium. Periodic updates may then be received from the user content preference identification device 106 and then stored in the user's media device 118 and/or in the other electronic device.

It should be emphasized that the above-described embodiments of the user content preference identification system 100 are merely possible examples of implementations of the invention. Many variations and modifications may be made to the above-described embodiments. All such modifications and variations are intended to be included herein within the scope of this disclosure and protected by the following claims.

The invention claimed is:

1. A method for recommending media content to a user based on emotions of the user, the method comprising:
   identifying an emotional state change of the user;
   receiving image information captured by an image capture device that is oriented in a direction of a visual field of view of the user when the emotional state change of the user is identified;
   identifying a first candidate object and a second candidate object in the captured image information, wherein the first and second candidate objects correspond to physical objects seen by the user at a time when the emotional state change of the user was identified;
   presenting a first object image to the user, wherein the first object image includes the first candidate object;
   presenting a second object image to the user, wherein the second object image includes the second candidate object; and receiving a response from the user indicating one of the first candidate object or the second candidate object precipitated the emotional state change of the user; and identifying one of a plurality of media content events as a recommended media content event based on the indicated one of the first candidate object or the second candidate object.

2. The method of claim 1, wherein identifying the emotional state change of the user is based on Electroencephalography (EEG) information corresponding to a plurality of brain wave lines of the user.

3. The method of claim 1, further comprising:
defining a keyword that describes the indicated one of the first candidate object or the second candidate object; and wherein identifying one of the plurality of media content events as a recommended media content event is based at least in part on the keyword.

4. The method of claim 1, wherein after identifying the emotional state change of the user, the method further comprising:
determining that an emotional state of the user is anticipation when the emotional state change of the user indicates that the user has an emotional feeling of excitement about an event that is going to happen, or is likely to happen, in the near future as a result of experiencing a first type of life event;
determining that the emotional state of the user is surprise when the emotional state change of the user indicates that the user has an emotional feeling of wonder, astonishment, or amazement as a result of experiencing a second type of life event that was unanticipated or that occurred unexpectedly;
determining that the emotional state of the user is joy when the emotional state change of the user indicates that the user has an emotional feeling of well-being, success, good fortune, or by the prospect of possessing what one desires as a result of experiencing a third type of life event;
determining that the emotional state of the user is sadness when the emotional state change of the user indicates that the user has an emotional feeling characterized by feelings of disadvantage, loss, despair, grief, helplessness, disappointment and sorrow as a result of experiencing a fourth type of life event;
determining that the emotional state of the user is disgust when the emotional state change of the user indicates that the user has an emotional feeling of revulsion or profound disapproval aroused by something unpleasant or offensive;
determining that the emotional state of the user is trust when the emotional state change of the user indicates that the user has an emotional feeling that someone is good and honest and will not harm the user, or that someone or something may be relied upon as a result of experiencing a sixth type of life event;
determining that the emotional state of the user is anger when the emotional state change of the user indicates that the user has an emotional feeling characterized by a strong feeling of annoyance, displeasure, or hostility as a result of experiencing a seventh type of life event;
determining that the emotional state of the user is fear when the emotional state change of the user indicates that the user has an emotional feeling of an unpleasant anticipation or awareness of danger, pain, or harm as a result of experiencing an eighth type of life event;

generating a media content event recommendation,
wherein the recommended media content event is indicated to the user as a media content event that the user is likely to enjoy in response to determining that the emotional state of the user is anticipation, joy, surprise or trust,
wherein the recommended media content event is indicated to the user as a media content event that the user is likely to dislike in response to determining that the emotional state of the user is sadness, disgust, anger or fear, and
wherein the recommended media content event is indicated to the user as a media content event that the user is likely to be disinterested in when determining that the emotional state of the user is not one of anticipation, surprise, joy, sadness, disgust, trust, anger, or fear; and
presenting the media content event recommendation to the user.

5. The method of claim 4, further comprising:
generating a user query that asks the user to specify their emotional state during the emotional state change of the user;
comparing the user's specified emotional state to the determined emotional state;
confirming that the determined emotional state is correctly determined when the determined emotional state is the same as the user's specified emotional state; and
changing the determined emotional state to the user's specified emotional state when the determined emotional state is different from the user's specified emotional state.

6. The method of claim 1, further comprising:
receiving audio information acquired by a microphone that includes sounds heard by the user while the image information is acquired by the image capture device; and
identifying a candidate sound in the audio information, wherein the candidate sound corresponds to a sound heard by the user during the emotional state change of the user,
wherein identifying one of the plurality of media content events as a recommended media content event is based on the identified candidate sound.

7. The method of claim 6, further comprising:
generating a user query that asks the user to confirm that the candidate sound precipitated the emotional state change of the user; and
receiving a user response that confirms that the sound caused the identified emotional state change of the user, wherein the recommended media content event is identified based on the confirmed candidate sound.

8. The method of claim 1, further comprising:
receiving eye orientation information acquired by an eye orientation sensor that senses eye orientation of the user while the image information is acquired by the image capture device, wherein the eye orientation information indicates an orientation of at least one eye of the user,
wherein identifying the first and second candidate objects in the captured image information is based on the orientation of the at least one eye of the user that indicates which ones of a plurality of objects the user was looking at that were within the visual field of view of the user when the image information was acquired.

9. A method for recommending media content to a user based on emotions of the user, the method comprising:
identifying an emotional state change of the user;

receiving image information captured by an image capture device that is oriented in a direction of a visual field of view of the user when the emotional state change of the user was identified;

identifying a candidate object in the captured image information, wherein the candidate object corresponds to a physical object seen by the user at a time when the emotional state change of the user was identified;

presenting an image of the candidate object to the user;

generating a user query that asks the user to specify an emotional state that they experienced during the identified emotional state change of the user; and receiving a user response that specified their emotional state that they experienced during the emotional state change, and identifying one of a plurality of media content events as a recommended media content event based on the user specified emotional state that they experienced during the emotional state change.

10. The method of claim 9, wherein identifying the emotional state change of the user is based on Electroencephalography (EEG) information corresponding to a plurality of brain wave lines of the user.

11. The method of claim 9, further comprising:

defining a keyword that describes the candidate object; and wherein identifying one of the plurality of media content events as a recommended media content event is based at least in part on the keyword.

12. The method of claim 9, wherein the candidate object identified in the captured image information is a first candidate object, wherein a second candidate object is also identified in the captured image information, and wherein prior to identifying one of the plurality of media content events as the recommended media content event, the method further comprising:

presenting a first object image to the user, wherein the first object image includes the first candidate object;

presenting a second object image to the user, wherein the second object image includes the second candidate object; and receiving a response from the user indicating that viewing one of the first candidate object or the second candidate object precipitated the emotional state change of the user, wherein identifying one of the plurality of media content events as the recommended media content event is based on the indicated one of the first candidate object or the second candidate object.

13. The method of claim 9, further comprising:

receiving audio information acquired by a microphone that includes sounds heard by the user while the image information is acquired by the image capture device; and identifying a candidate sound in the audio information, wherein the candidate sound corresponds to a sound heard by the user during the emotional state change of the user, wherein identifying one of the plurality of media content events as a recommended media content event is based on the identified candidate sound.

14. The method of claim 13, further comprising:

generating a user query that asks the user to confirm that the candidate sound precipitated the emotional state change of the user; and receiving a user response that confirms that the sound caused the identified emotional state change of the user, wherein the recommended media content event is identified based on the confirmed candidate sound.

15. The method of claim 9, further comprising:

receiving eye orientation information acquired by an eye orientation sensor that senses eye orientation of the user while the image information is acquired by the image capture device, wherein the eye orientation information indicates an orientation of at least one eye of the user, wherein identifying the candidate object in the captured image information is based on the orientation of the at least one eye of the user that indicates which one of a plurality of objects the user was looking at that were within the visual field of view of the user when the image information was acquired.

16. A method for recommending media content to a user based on emotions of the user, the method comprising:

identifying an emotional state change of the user;

receiving image information captured by an image capture device that is oriented in a direction of a visual field of view of the user when the emotional state change of the user was identified;

identifying a candidate object in the captured image information, wherein the candidate object corresponds to a physical object seen by the user at a time when the emotional state change of the user was identified; and receiving audio information acquired by a microphone that includes sounds heard by the user while the image information is acquired by the image capture device;

identifying a candidate sound in the audio information, wherein the candidate sound corresponds to a sound heard by the user during the emotional state change of the user;

generating a user query that asks the user to select one of the candidate object or the candidate sound as precipitating the change in the user's emotional state during the emotional state change of the user;

receiving a user response from the user that is a selection of one of the candidate object or the candidate sound;

identifying one of a plurality of media content events as a recommended media content event based on the candidate object when the user selects the candidate object; and identifying one of the plurality of media content events as a recommended media content event based on the candidate sound when the user selects the candidate sound.

17. The method of claim 16, wherein identifying the emotional state change of the user is based on Electroencephalography (EEG) information corresponding to a plurality of brain wave lines of the user.

18. The method of claim 16, further comprising:

defining a keyword that describes the selected one of the candidate sound or the candidate object; and wherein identifying one of the plurality of media content events as a recommended media content event is based at least in part on the keyword.

19. The method of claim 16, further comprising:

receiving eye orientation information acquired by an eye orientation sensor that senses eye orientation of the user while the image information is acquired by the image capture device, wherein the eye orientation information indicates an orientation of at least one eye of the user, wherein identifying the candidate object in the captured image information is based on the orientation of the at least one eye of the user that indicates which one of a plurality of objects the user was looking at that were within the visual field of view of the user when the image information was acquired.

20. The method of claim 16, further comprising:

generating a user query that asks the user to specify an emotional state that they experienced during the identified emotional state change of the user; and receiving a user response that specified their emotional state that they experienced during the emotional state change, wherein one of the plurality of media content events is identified as the recommended media content event based on the user specified emotional state that they experienced during the emotional state change.

\* \* \* \* \*

UNITED STATES PATENT AND TRADEMARK OFFICE
CERTIFICATE OF CORRECTION

PATENT NO. : 11,323,776 B2
APPLICATION NO. : 16/991003
DATED : May 3, 2022
INVENTOR(S) : Newell et al.

It is certified that error appears in the above-identified patent and that said Letters Patent is hereby corrected as shown below:

In the Claims

Claim 1, Column 41, Line 1, after "indicating" insert --which--

Signed and Sealed this
Fourteenth Day of June, 2022

Katherine Kelly Vidal
*Director of the United States Patent and Trademark Office*